US010631977B2

(12) United States Patent
Tayeb et al.

(10) Patent No.: US 10,631,977 B2
(45) Date of Patent: Apr. 28, 2020

(54) COVERING AND ASSEMBLY METHOD FOR TRANSCATHETER VALVE

(71) Applicant: Edwards Lifesciences Corporation, Irvine, CA (US)

(72) Inventors: Liron Tayeb, Peduel (IL); Ilan Tamir, Hefzi-Bah (IL)

(73) Assignee: Edwards Lifesciences Corporation, Irvine, CA (US)

( * ) Notice: Subject to any disclaimer, the term of this patent is extended or adjusted under 35 U.S.C. 154(b) by 215 days.

(21) Appl. No.: 15/240,570

(22) Filed: Aug. 18, 2016

(65) Prior Publication Data
US 2017/0056163 A1  Mar. 2, 2017

Related U.S. Application Data

(60) Provisional application No. 62/209,180, filed on Aug. 24, 2015.

(51) Int. Cl.
A61F 2/24 (2006.01)

(52) U.S. Cl.
CPC .......... *A61F 2/2409* (2013.01); *A61F 2/2415* (2013.01); *A61F 2/2418* (2013.01); *A61F 2220/0075* (2013.01); *A61F 2230/0091* (2013.01); *A61F 2250/006* (2013.01); *A61F 2250/0069* (2013.01)

(58) Field of Classification Search
CPC ........ A61F 2/24; A61F 2/2412; A61F 2/2418; A61F 2/243; A61F 2/2469
See application file for complete search history.

(56) References Cited

U.S. PATENT DOCUMENTS

| 3,983,581 A | 10/1976 | Angell et al. |
| 5,258,023 A | 11/1993 | Reger |
| 5,336,258 A | 8/1994 | Quintero et al. |
| 5,628,786 A | 5/1997 | Banas et al. |
| 5,776,188 A | 7/1998 | Shepherd et al. |

(Continued)

FOREIGN PATENT DOCUMENTS

| WO | 9640012 A1 | 12/1996 |
| WO | 2012/142189 A1 | 10/2012 |
| WO | 2015023862 A2 | 2/2015 |

OTHER PUBLICATIONS

Int'l. Search Report for PCT/US2016/048028, dated Nov. 1, 2016.

*Primary Examiner* — Bruce E Snow
(74) *Attorney, Agent, or Firm* — Lewis Roca Rothgerber Christie LLP; Joel B. German

(57) ABSTRACT

A covering layer for a transcatheter heart valve is in various embodiments configured to prevent or reduce damage to the native valve tissue around the site where the prosthetic valve is implanted. In some cases, prosthetic valves are manufactured with the covering layer attached. Other covering layers are stand-alone accessories that can be mounted onto pre-existing prosthetic valves by an end user. Covering layers that can be mounted by an end user are provided with various features that can facilitate easier attachment of the covering layer to the prosthetic valve, which further reduces the possibility of damage to the covering layer or to the valve. Another covering is provided with two layers in order to insulate and protect the native tissue surrounding the implant from damage due to friction or abrasion, and/or other movement driven wear.

16 Claims, 15 Drawing Sheets

(56) References Cited

U.S. PATENT DOCUMENTS

| | | |
|---|---|---|
| 5,843,161 A | 12/1998 | Solovay |
| 5,957,949 A | 9/1999 | Leonhardt et al. |
| 6,015,431 A | 1/2000 | Thornton et al. |
| 6,110,198 A | 8/2000 | Fogarty et al. |
| 6,306,164 B1 | 10/2001 | Kujawski |
| 6,352,554 B2 | 3/2002 | De Paulis |
| 6,482,228 B1 | 11/2002 | Norred |
| 6,585,766 B1 | 7/2003 | Huynh et al. |
| 6,729,356 B1 | 5/2004 | Baker et al. |
| 6,814,754 B2 | 11/2004 | Greenhalgh |
| 6,904,909 B2 | 6/2005 | Andreas et al. |
| 6,911,040 B2 | 6/2005 | Johnson et al. |
| 7,018,406 B2 | 3/2006 | Seguin et al. |
| 7,147,663 B1 | 12/2006 | Berg et al. |
| 7,175,652 B2 | 2/2007 | Cook et al. |
| 7,192,441 B2 | 3/2007 | Sherry |
| 7,264,632 B2 | 9/2007 | Wright et al. |
| 7,993,394 B2 | 8/2011 | Hariton et al. |
| 8,142,492 B2 | 3/2012 | Forster et al. |
| 8,808,356 B2 | 8/2014 | Braido et al. |
| 8,845,722 B2 | 9/2014 | Gabbay |
| 8,979,922 B2 | 3/2015 | Jayasinghe et al. |
| 8,992,608 B2 | 3/2015 | Haug et al. |
| 9,220,594 B2 | 12/2015 | Braido et al. |
| 2001/0027338 A1 | 10/2001 | Greenberg |
| 2003/0074058 A1 | 4/2003 | Sherry |
| 2003/0236567 A1 | 12/2003 | Elliot |
| 2005/0137687 A1 | 6/2005 | Salahieh et al. |
| 2009/0099653 A1 | 4/2009 | Suri et al. |
| 2010/0204781 A1* | 8/2010 | Alkhatib ............... A61F 2/2418 623/1.26 |
| 2012/0035719 A1 | 2/2012 | Forster et al. |
| 2014/0214159 A1* | 7/2014 | Vidlund ................. A61L 27/34 623/2.14 |
| 2014/0277390 A1 | 9/2014 | Ratz et al. |
| 2015/0230921 A1 | 8/2015 | Chau et al. |

\* cited by examiner

COVERING AND ASSEMBLY METHOD FOR TRANSCATHETER VALVE

CROSS-REFERENCE TO RELATED APPLICATION(S)

The present application claims priority to and the benefit of U.S. Provisional Patent Application Ser. No. 62/209,180, filed Aug. 24, 2015, the contents of which are hereby incorporated by reference in their entirety.

BACKGROUND

Field

The invention relates generally to medical devices and procedures pertaining to prosthetic heart valves. More specifically, the invention relates to replacement of heart valves that have malformations and/or dysfunctions. Embodiments of the invention relate to prosthetic heart valves for replacing a mitral valve in the heart, or for replacing other valves where an additional ring or other anchor is utilized together with the prosthetic heart valve at the implant site, and assembly methods for preparing such prosthetic heart valves for implantation.

Description of Related Art

Referring first generally to FIGS. 1 and 2, the mitral valve controls the flow of blood between the left atrium and the left ventricle of the human heart. After the left atrium receives oxygenated blood from the lungs via the pulmonary veins, the mitral valve permits the flow of the oxygenated blood from the left atrium into the left ventricle. When the left ventricle contracts, the oxygenated blood held in the left ventricle is delivered through the aortic valve and the aorta to the rest of the body. Meanwhile, the mitral valve closes during ventricular contraction, to prevent the flow of blood back into the left atrium.

When the left ventricle contracts, the blood pressure in the left ventricle increases substantially, and urges the mitral valve closed. Due to the large pressure differential between the left ventricle and the left atrium during ventricular contraction, a possibility of prolapse, or eversion of the leaflets of the mitral valve back into the atrium, arises. To prevent this, a series of chordae tendineae connect the mitral valve to the papillary muscles along opposing walls of the left ventricle. The chordae tendineae are schematically illustrated in both the heart cross-section of FIG. 1 and the top view of the mitral valve in FIG. 2. Just before and during ventricular contraction, the papillary muscles also contract and maintain tension in the chordae tendineae, to hold the leaflets of the mitral valve in the closed position and preventing them from turning inside-out and back into the atrium, thereby also preventing backflow of the oxygenated blood into the left atrium.

Complications of the mitral valve can potentially cause fatal heart failure. One form of valvular heart disease is mitral valve leak, also known as mitral regurgitation, characterized by the abnormal leaking of blood from the left ventricle back into the left atrium through the mitral valve. In these circumstances, it may be desirable to repair the mitral valve or to replace the functionality of the mitral valve with that of a prosthetic heart valve.

Up to this point, mitral valve repair has been more popular than valve replacement, since there were previously little or no effective commercially available ways to replace a mitral valve through catheter implantation and/or other minimal or less invasive procedures.

Replacement of a mitral valve is difficult in many respects, for example, due to the physical structure of the valve and difficulties in accessing the valve. The most prominent obstacle for mitral valve replacement is anchoring or retaining the valve in position, due to the valve being subject to a large cyclic load. Especially during ventricular contraction, the movement of the heart and the load on the valve can combine to shift or dislodge a prosthetic valve. Also, the movement and rhythmic load can fatigue materials, leading to fractures of the implanted valve. If the orientation of a mitral prosthesis is unintentionally shifted, blood flow between the left atrium and the left ventricle can be obstructed or otherwise negatively affected. While puncturing the tissue in or around the mitral valve annulus to better anchor an implanted valve is an option for retaining the placement of the implant, this can potentially lead to unintended perforation of the heart and patient injury.

Another issue with mitral valve replacement is the size and shape of the native mitral valve. A general shape of the mitral valve and its leaflets as seen from the left atrium is illustrated in FIG. 2. The mitral valve annulus is quite large and non-circular, when compared for example, to the more circular aortic valve annulus, where valve replacement is more prominent. As such, a circular prosthetic mitral valve that is too small can cause leaks around the implanted valve (i.e., paravalvular leak) if a good seal is not established around the valve. Meanwhile, a circular valve implant that is too large can stretch out and damage the native valve annulus.

SUMMARY

Since many valves have been developed for the aortic position, it would be desirable to try to take advantage of these existing valve technologies and to utilize the same or similar valves in mitral valve replacements. One way of utilizing these preexisting prosthetic valves at the mitral position is to use the prosthetic valves together with an anchor or other docking station that will form a more appropriately shaped implant site at the mitral valve annulus, so that the prosthetic valves can be implanted more securely, while reducing or eliminating leakage around the valve after implantation. For example, a mitral anchor or docking station can form a more circular bore to more closely match the circular profiles of existing valve implants. In this manner, an existing valve implant developed for the aortic position, perhaps with some modification, could then be implanted at the mitral position together with such an anchor. Some existing valves can even fit well with little or no modification, such as the Edwards Lifesciences Sapien XT™ valve.

Anchors or docking stations for anchoring prosthetic valves at the mitral position can include, for example, rings or coils that wrap around portions of the native mitral valve or surrounding tissue, to form a more circular or cylindrical surface against which a prosthetic valve can expand. The anchors can wrap around, for example, the native mitral leaflets, the chordae tendineae, and/or other surrounding tissue. Since the prosthetic heart valve is expanded inside the mitral valve annulus, native tissue is sandwiched between the valve frame and the anchor. The use of a prosthetic heart valve with a bare metal frame, together with an anchoring ring or coil, can lead to damage to the native tissue that is pinched between the valve and the anchor. For example, friction between the surrounding native valve tissue with the apices, corners, or various other edges on the valve frame can damage the tissue and lead, for example, to paravalvular leakage.

Features of the invention provide prosthetic heart valves that can be implanted with existing anchors or docking stations at the mitral position, and that will prevent or reduce damage to the surrounding native valve tissue after implantation. Embodiments of the invention provide devices and methods for preparing prosthetic heart valves for mitral valve replacement. The devices and methods can prevent or reduce regurgitation or leaking of blood around the replacement prosthesis at the time of implantation, as well as prevent or reduce damage to the native valve tissue over time, which will also lead to less paravalvular leakage in and around the implanted prosthesis long after the prosthetic valve has been implanted.

In an embodiment of the invention, a transcatheter heart valve includes a valve prosthesis including a radially expandable and collapsible frame and a plurality of valve leaflets positioned at least partially in the frame and configured to control blood flow through the valve prosthesis. The frame has a first end, a second end, and an outer surface extending from the first end to the second end, and a covering connected to the valve prosthesis. The covering covers at least the first end and substantially all of the outer surface of the frame.

In another embodiment of the invention, a covering is provided for a valve prosthesis including a frame and a plurality of valve leaflets positioned at least partially in the frame and configured to control blood flow through the valve prosthesis, wherein the frame has a first end defining an outflow end, a second end defining an inflow end, and an outer surface extending from the first end to the second end. The covering includes a covering layer configured to cover at least the outer surface of the frame at the first end and a plurality of strings connected to the covering layer, the strings configured to facilitate attachment of the covering layer to the valve prosthesis.

In yet another embodiment of the invention, a system includes a valve prosthesis including a radially expandable and collapsible frame and a plurality of valve leaflets positioned at least partially in the frame and configured to control blood flow through the valve prosthesis, wherein the frame has a first end defining an outflow end, a second end defining an inflow end, and an outer surface extending from the first end to the second end, and a covering separate from and attachable to the valve prosthesis for covering at least the outer surface of the frame at the first end, the covering comprising at least one string configured to facilitate attachment of the covering to the valve prosthesis.

In still another embodiment of the invention, a method is provided for attaching a covering on a valve prosthesis, the valve prosthesis including a frame and a plurality of valve leaflets positioned at least partially in the frame and configured to control blood flow through the valve prosthesis, wherein the frame has a first end, a second end, and an outer surface extending from the first end to the second end, the covering including a covering layer and a plurality of loops. The method includes mounting the covering layer around the outer surface of the valve prosthesis and attaching the covering layer to the valve prosthesis using the plurality of loops.

According to embodiments of the invention, mitral valve replacement can be more effectively realized by providing measures to better protect the surrounding native valve tissue during and after implantation, through a variety of different implementation approaches.

BRIEF DESCRIPTION OF THE DRAWINGS

Further features and advantages of the invention will become apparent from the description of embodiments using the accompanying drawings. In the drawings.

DETAILED DESCRIPTION

Disclosed herein are prosthetic heart valves, and methods of manufacturing or preparing the prosthetic heart valves for implantation, that allow for prevention or reduction in damage to the native valve tissue surrounding the prosthesis or that come into contact with the prosthesis after implantation into a patient. By providing a more robust seal around the prosthetic implant, leakage in and around the implant can be greatly reduced, and performance of the valve can be improved.

Figure 1:
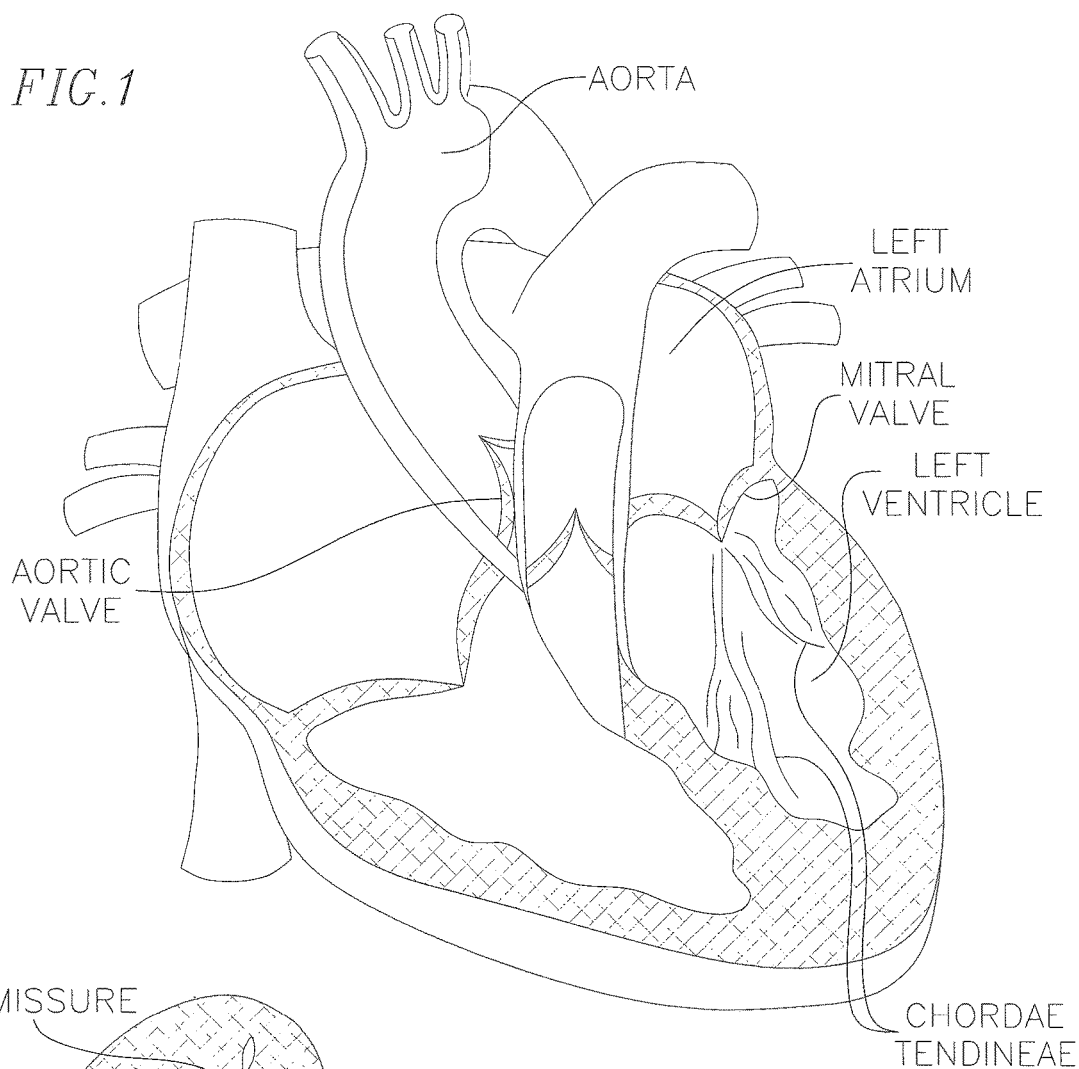
FIG. 1 shows a schematic cross-sectional view of a human heart.
Figure 2:
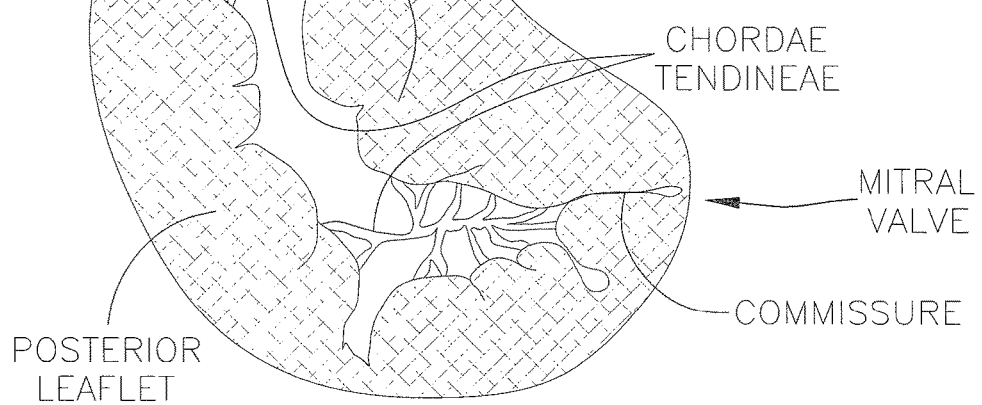
FIG. 2 shows a schematic top view of the mitral valve annulus of a heart.
Figure 3:
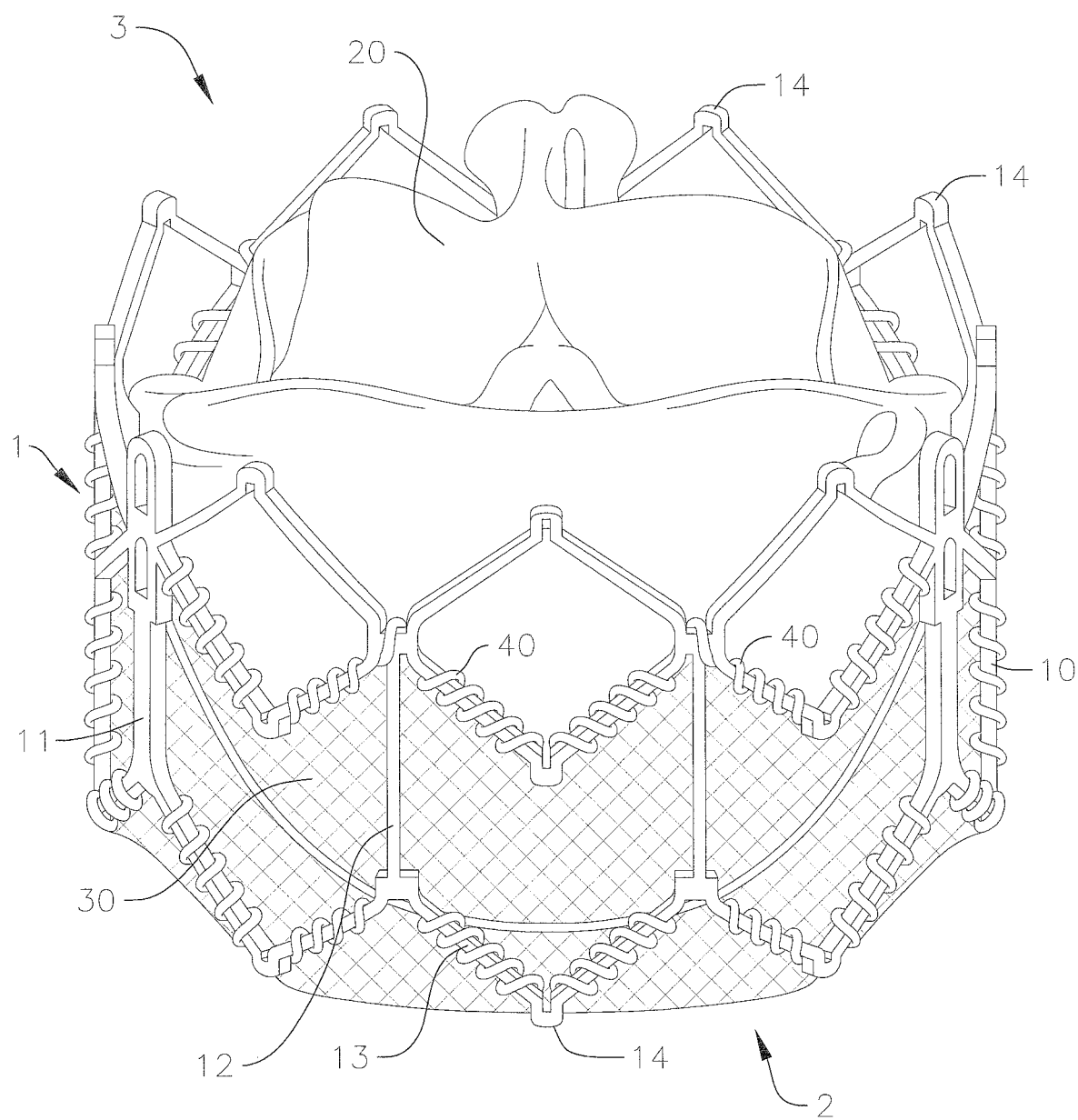
FIG. 3 shows a perspective view of an embodiment of a prosthetic heart valve.

Some transcatheter heart valves are designed to be radially crimped to facilitate endovascular delivery to an implant site at a patient's heart. Once positioned at a native valve annulus, the replacement valve is then expanded to an operational state, for example, by an expansion balloon. One embodiment of a prosthetic heart valve is illustrated in FIG. 3. A transcatheter heart valve with a valve profile similar to the prosthetic valve shown in FIG. 3 is the Edwards Lifesciences SAPIEN XT™ valve. The prosthetic valve 1 in FIG. 3 has an inflow end 2 and an outflow end 3, and includes a frame or stent 10 and a leaflet structure 20 supported inside the frame 10. In some embodiments, a skirt 30 can be attached to an inner surface of the frame 10 to form a more suitable attachment surface for the valve leaflets of the leaflet structure 20.

The frame 10 can be made of any body compatible expandable material that permits both crimping to a radially collapsed state and expansion back to the expanded state illustrated in FIG. 3. The frame 10 can also be made of, for example, Nitinol or another self-expanding material. Other suitable materials can also be used.

The frame 10 is an annular structure having a plurality of vertically extending commissure attachment posts 11, which attach and help shape the leaflet structure 20 therein. Additional vertical posts or struts 12, along with circumferentially extending strut sections 13, help form the rest of the frame 10. The strut sections 13 of the frame 10 zig-zag and form edged crown portions or apices 14 at the inflow and outflow ends 2, 3 of the valve 1. Furthermore, the attachment posts 11 can also form edges at one or both ends of the frame 10.

In prosthetic valve 1, the skirt 30 is attached to an inner surface of the valve frame 10 via one or more threads 40, which generally wrap around to the outside of various struts 11, 12, 13 of the frame 10, as needed. The skirt 30 provides a more substantive attachment surface for portions of the leaflet structure 20 positioned closer to the inflow end 2 of the valve 1.

Figure 4A:
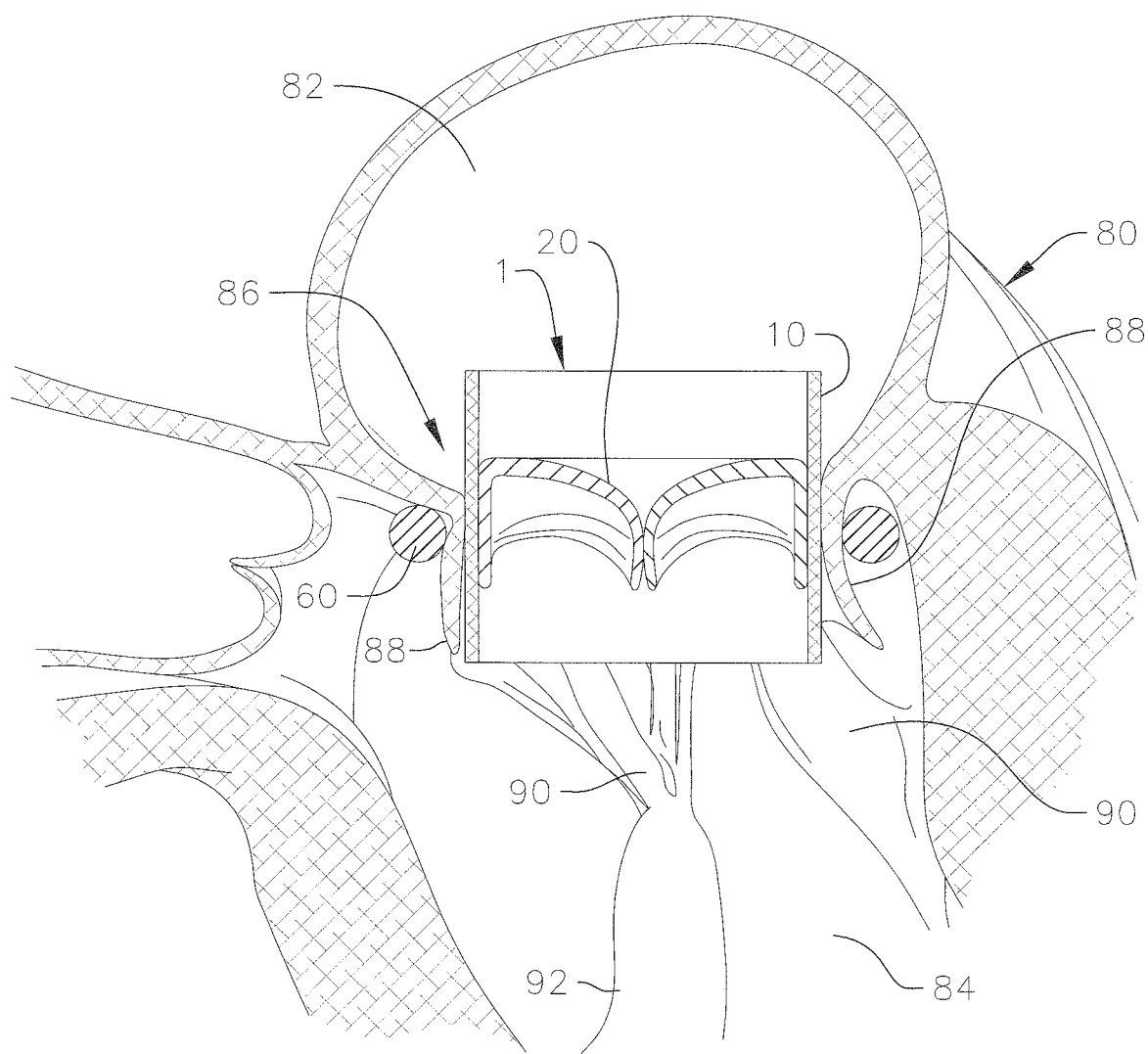
FIG. 4A shows a side cross-sectional view of a ring anchor deployed in a mitral position of the heart, with an implanted valve prosthesis, according to an embodiment of the invention.
Figure 4B:
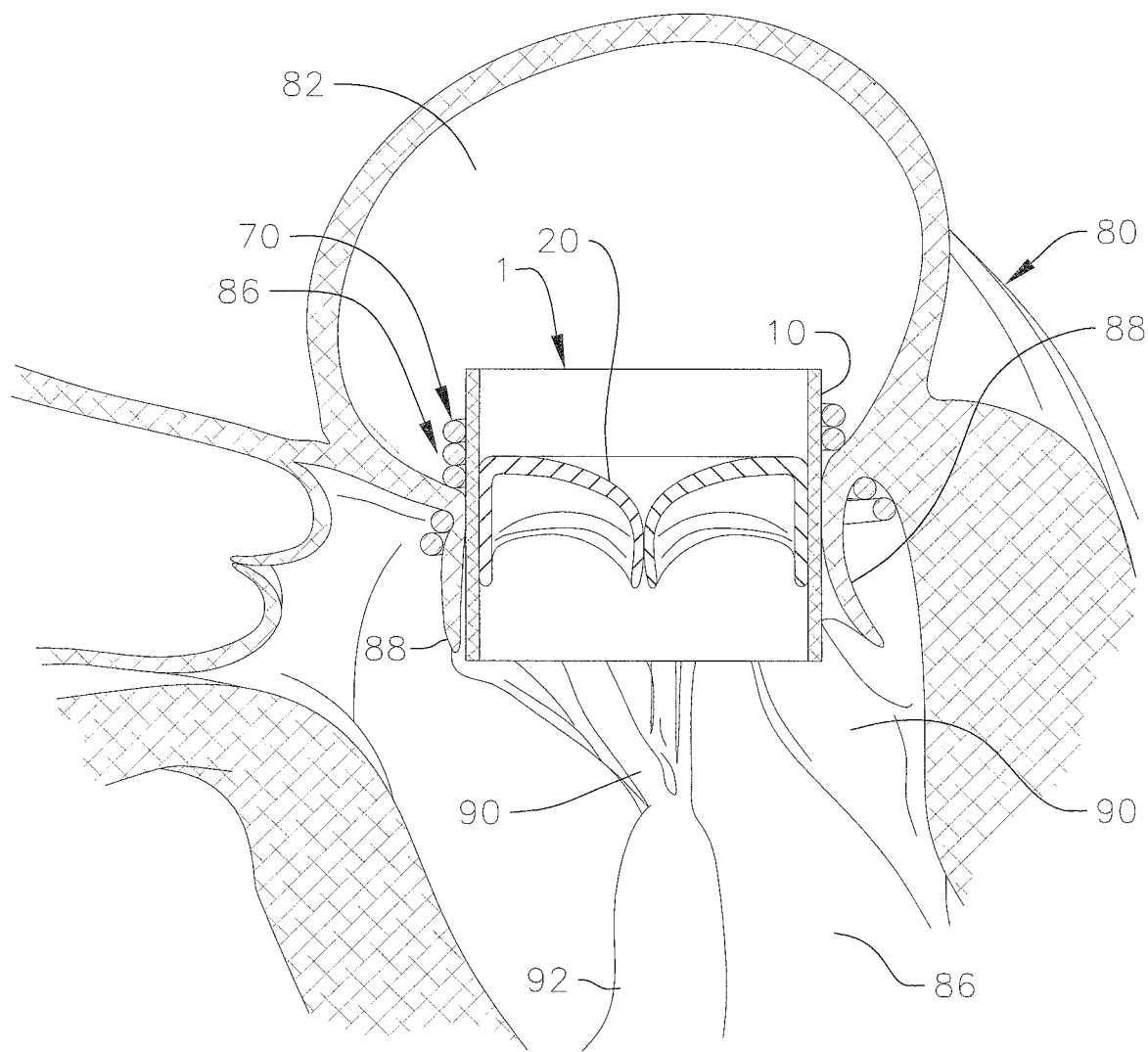
FIG. 4B shows a side cross-sectional view of a coil anchor deployed in the mitral position of the heart, with an implanted valve prosthesis, according to another embodiment of the invention.

FIGS. 4A and 4B show side cross-sectional views of embodiments of different anchors that can be used to facilitate implantation of the valve 1 at the mitral position of a patient's heart. As shown in FIGS. 4A and 4B, a left side of a heart 80 includes a left atrium 82, a left ventricle 84, and a mitral valve 86 connecting the left atrium 82 and the left ventricle 84. The mitral valve 86 includes anterior and posterior leaflets 88 that are connected to an inner wall of the left ventricle 84 via chordae tendineae 90 and papillary muscles 92.

In FIG. 4A, a first anchoring device includes a flexible ring or halo 60 that surrounds the native leaflets 88 of the mitral valve 86 and/or the chordae tendineae 90. The ring 60 pinches or urges portions of the leaflets inwards, in order to form a more circular opening at the mitral position, for more effective implantation of the prosthetic valve 1. The valve prosthesis 1 is retained in the native mitral valve annulus 86 by the ring anchor 60, and can be delivered to the position shown, for example, by positioning the valve 1 in the mitral annulus 86 while the valve 1 is crimped, and then expanding the valve 1 once it is positioned as shown in FIG. 4A. Once expanded, the valve 1 pushes outwardly against the ring anchor 60 to secure the positions of both the valve 1 and the ring anchor 60. In some embodiments, an undersized ring anchor 60 with an inner diameter that is slightly smaller than the diameter of the prosthetic valve 1 in its expanded state can be used, to provide stronger friction between the parts, leading to more secure attachment. As can be seen in FIG. 4A, at least a portion of the native mitral valve leaflets 88 and/or a portion of the chordae tendineae 90 are pinched or sandwiched between the valve 1 and the ring anchor 60.

FIG. 4B is similar to FIG. 4A, except instead of a ring anchor 60, a helical anchor 70 is utilized instead. The helical anchor 70 can include more coils or turns than the ring anchor 60, and can extend both upstream and downstream of the mitral valve annulus 86. The helical anchor 70 in some situations can provide a greater and more secure attachment area against which the valve 1 can abut. Similar to the ring anchor 60 in FIG. 4A, at least a portion of the native mitral valve leaflets 88 and/or the chordae 90 are pinched between the valve 1 and the helical anchor 70.

As discussed above, prosthetic valve 1 generally includes a metal frame 10 that forms a number of edges. In addition, many frames 10 are constructed with edged crowns or apices 14 and protruding commissure attachment posts 11, as well as threads 40 that can be exposed along an outer surface of the frame 10. These features can cause damage to the native mitral tissue that is lodged between the prosthetic valve 1 and the anchor 60, 70, for example, by movement or friction between the native tissue and the various abrasive surfaces of the prosthetic valve 1. In addition, other native tissue in close proximity to the prosthetic valve 1 can also potentially be damaged.

Figure 5:
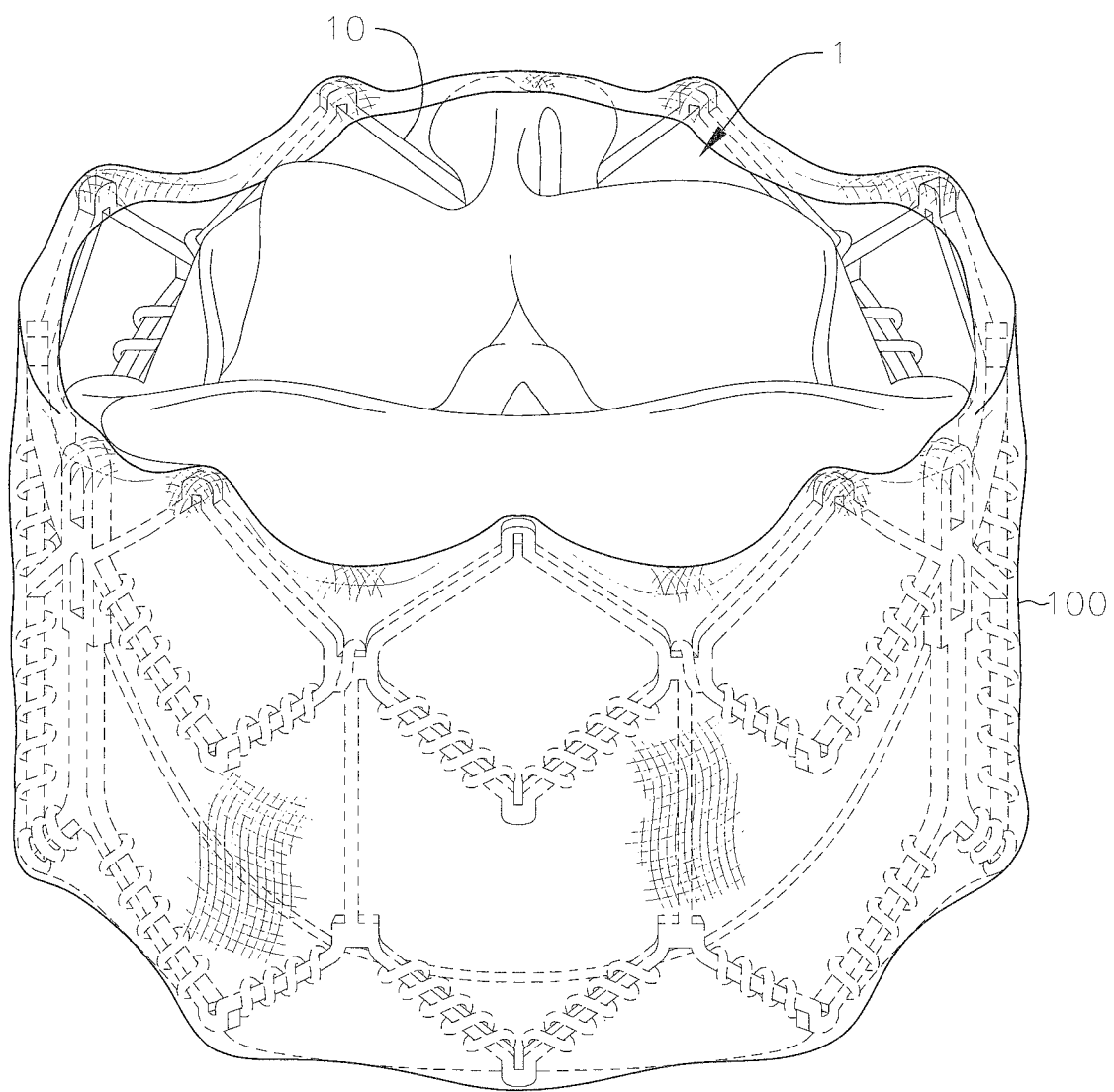
FIG. 5 shows a perspective view of the prosthetic heart valve of FIG. 3, with a casing or covering wrapped around the prosthesis, according to a first embodiment of the invention.

A prosthetic heart valve according to an embodiment of the invention is illustrated in FIG. 5. FIG. 5 shows the prosthetic heart valve 1 wrapped in a casing or covering 100. The covering 100 covers substantially an entire outer surface of the valve frame 10, so that the native heart tissue around the valve prosthesis 1 is protected from the various edges and other abrasive surfaces of the valve 1, without affecting functionality of the valve leaflets 20 housed inside the frame 10. In one embodiment, the covering 100 is made of a biocompatible cloth or other similar material. In another embodiment, pericardial tissue or patches or other similar material can be used as the covering 100 to cover the entire valve 1 or portions of the outer surface of valve 1 with exposed edges, abrasive materials, or other harmful surfaces. Such coverings 100 can be sewn or otherwise attached to the outside of the valve frame 10, and can serve to reduce the friction between the valve 1 and the surrounding native tissue at the implant site.

The covering 100 can be added to the outer surface of the prosthetic valve 1 during manufacturing. However, such an approach would involve changing the manufacturing processes and equipment needed to make the valve. Furthermore, adding a covering to existing valves at the manufacturing stage essentially creates a new valve that would likely have to undergo a new set of extensive and long term quality assurance and regulatory testing before the valve can be brought to market. This approach would be time consuming and incur a great deal of resources.

Figure 6:
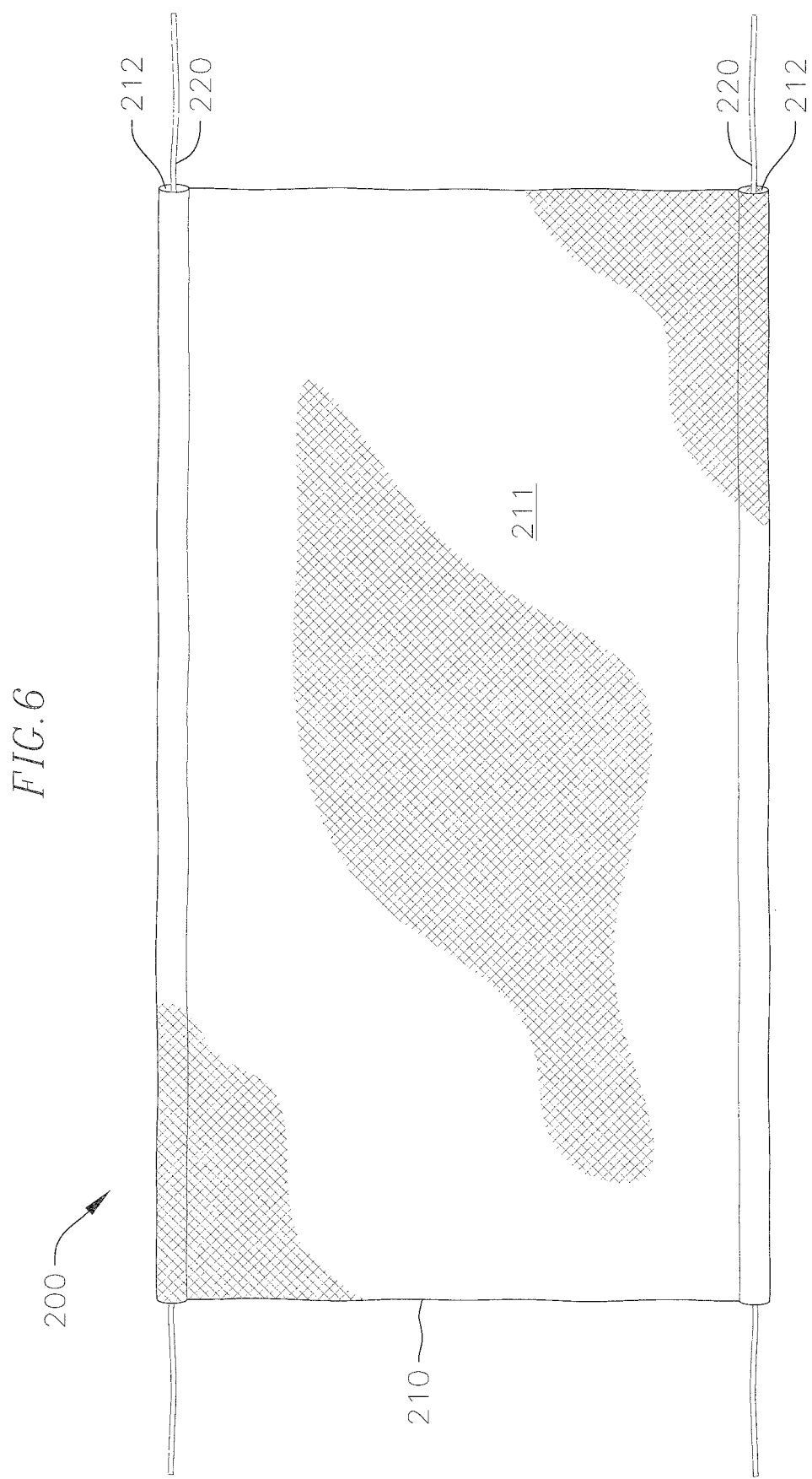
FIG. 6 shows a covering for a heart valve according to a second embodiment.
Figure 7:
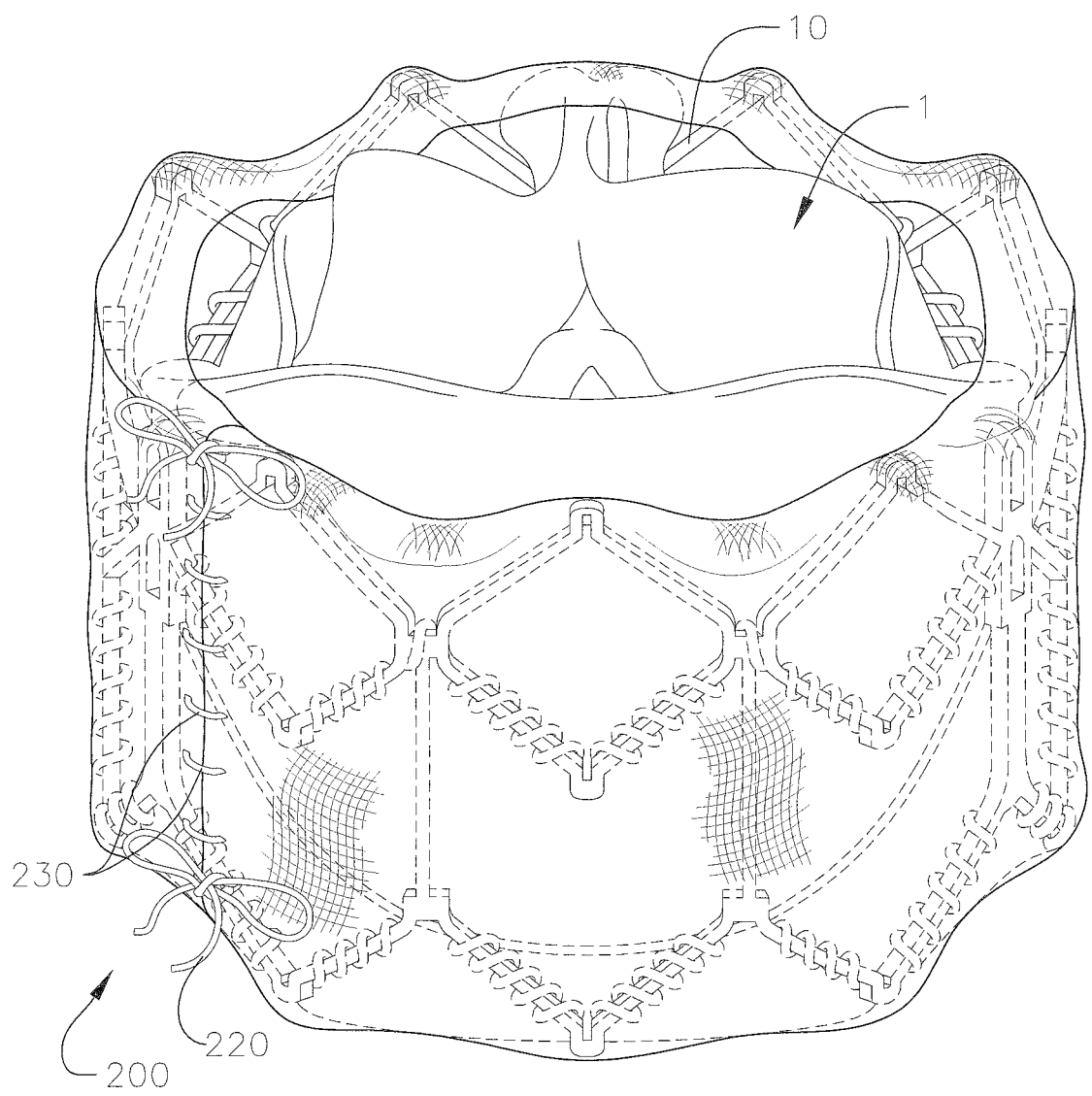
FIG. 7 shows a perspective view of a prosthetic heart valve with the covering of FIG. 6 wrapped around the prosthesis.

An alternative approach is provided in the embodiment illustrated in FIGS. 6 and 7. FIGS. 6 and 7 show a second embodiment of the invention, which includes a casing or covering 200 that is a stand-alone accessory that can be attached to an existing valve prosthesis by a practitioner or other end user. A main body 210 of the covering 200 can be made of a biocompatible cloth or other suitable biocompatible material with low friction and low abrasive properties.

The cloth or other material used for the body 210 can be constructed of a stretchable material, possibly a knitted or otherwise breathable material, and/or a material that will promote ingrowth after implantation. The body 210 of the covering 200 is a generally rectangular cloth with a central portion 211 sized and shaped to wrap around the entire prosthetic valve 1 in a circumferential direction. The body 210 further includes loop portions 212 on one or both ends of the central portion 211, that will be positioned approximate the inflow and outflow ends 2, 3 of the prosthetic valve 1. The loop portions 212 can be formed, for example, by folding over and sewing down or otherwise connecting the top and bottom ends of the body 210 to form small overlapping regions defining sleeves or passageways. The loop portions 212 can also be formed using various other methods. The covering 200 further includes one or more strings or threads 220 that are held in the loop portions 212 and that extend out of ends of the loop portions 212. Some embodiments of the covering 200 do not include loop portions 212, where the strings or threads 220 in these embodiments are instead sewn directly to portions of the body 210, as needed, in order to securely attach the threads 220 to the body 210.

As seen in FIG. 7, the covering 200 can be wrapped or dressed around an outer surface of an existing prosthetic valve 1 by a practitioner or other end user, and ends of each of the threads 220 can be tightened and tied together using any appropriate suturing or tying technique, to keep the covering 200 attached to the valve 1. The threads 220 can be used to further tighten the ends of the covering 200 so that the covering 200 forms or defines slightly smaller or narrower end openings or perimeters than the inflow and outflow ends 2, 3 of the valve 1. In this manner, the corners or apices 14 of the frame and/or ends of the commissure attachment posts 11 can also be covered by the covering 200, to better protect the surrounding heart tissue from being cut, abraded or otherwise damaged by the ends of the valve frame 10. In some embodiments, the end user can further sew or otherwise more securely attach the meeting ends of the covering 200 with additional threads 230, to form an even more secure attachment between the covering 200 and the valve prosthesis 1.

By providing a protective coat or covering 200 that is a separate accessory according to the second embodiment shown in FIGS. 6 and 7, and that can be easily attached to an existing prosthetic valve 1 by a practitioner prior to implantation, the covering can more easily be brought to market. Furthermore, coverings can be designed and modified in various different manners to facilitate easier attachment by end users.

Figure 8A:
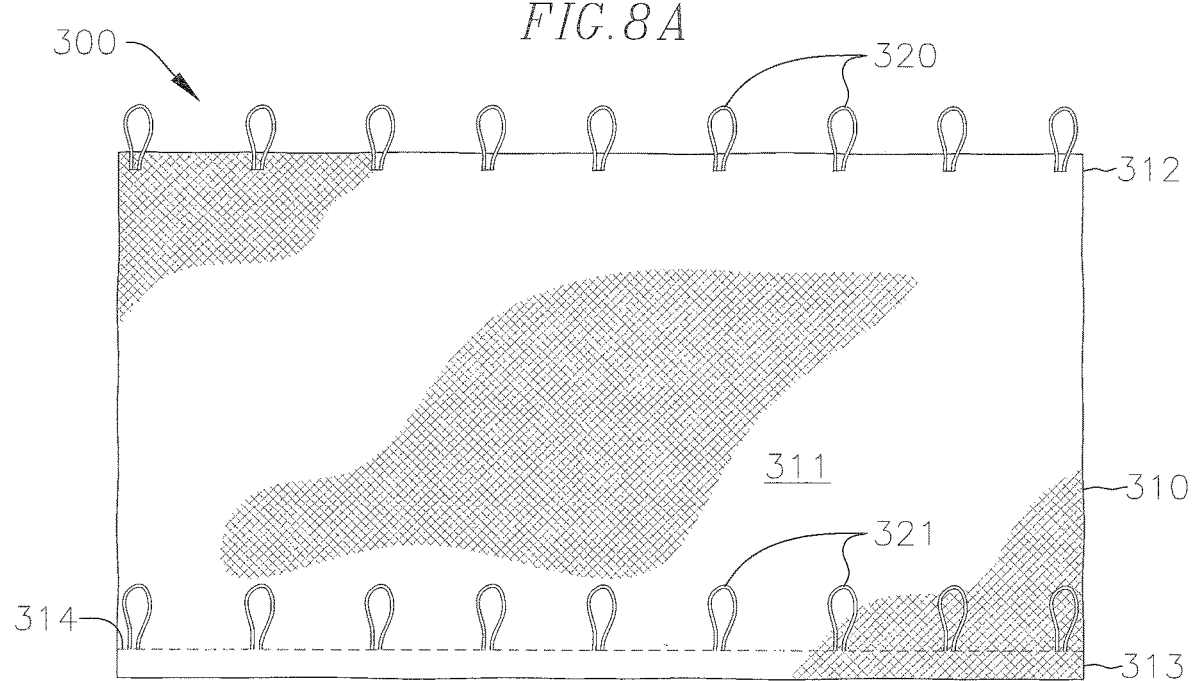
FIGS. 8A and 8B show a covering for a heart valve according to a third embodiment, before and after a final manufacturing step, respectively.
Figure 8B:
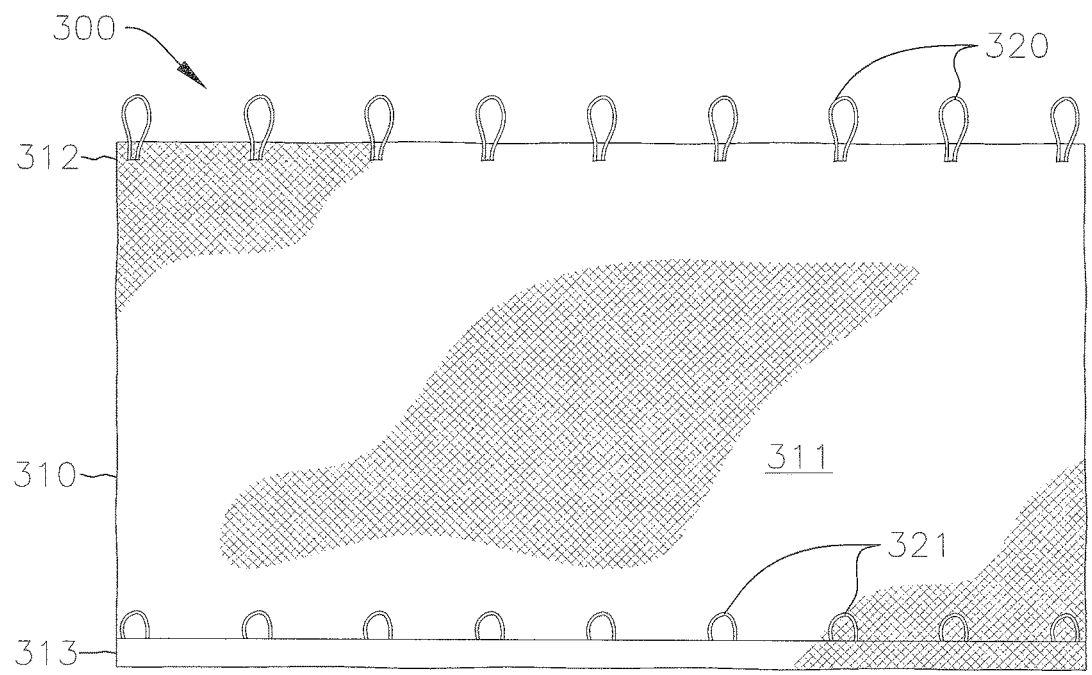
Figure 9:
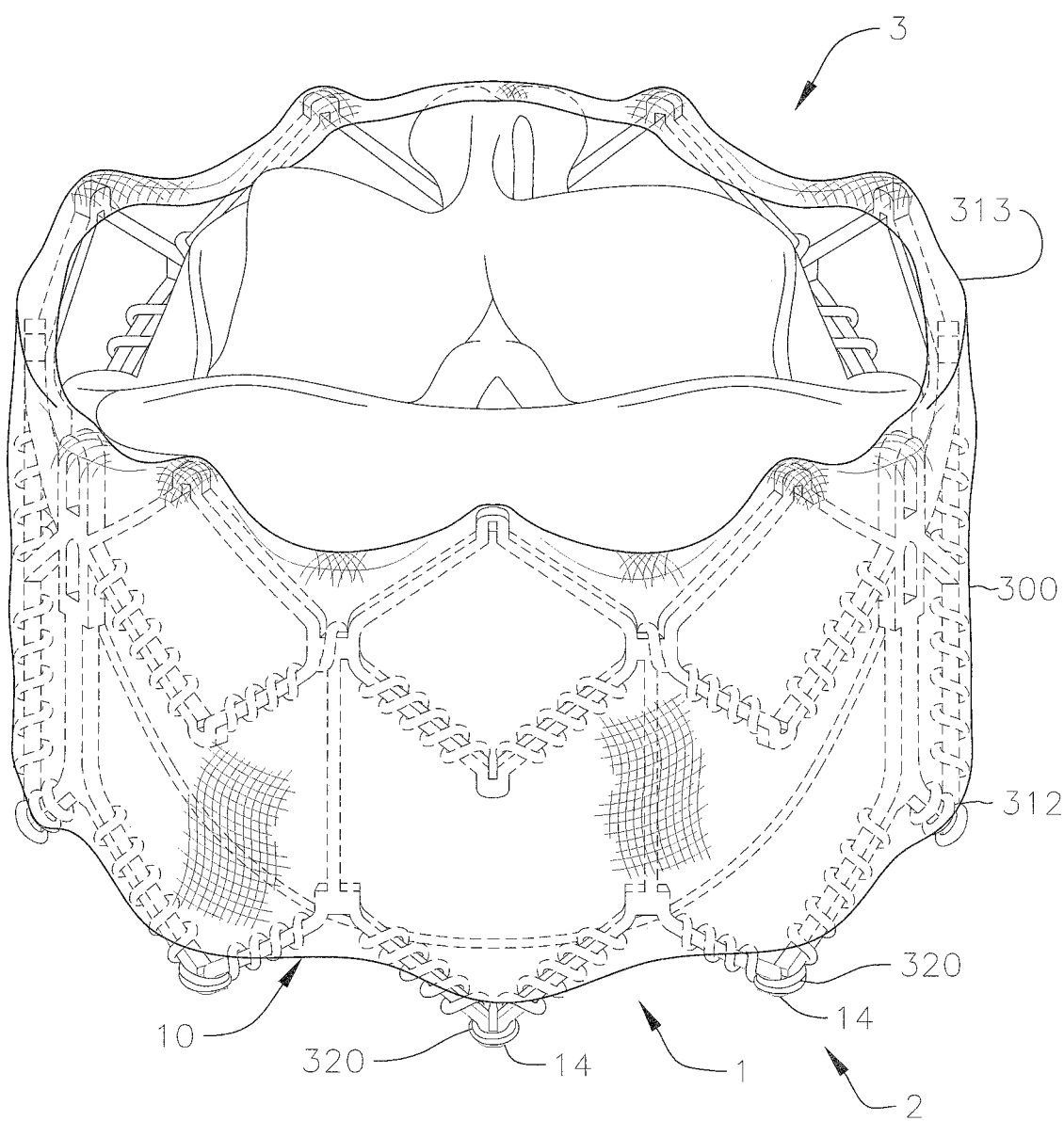
FIG. 9 shows a perspective view of a prosthetic heart valve with the covering of FIGS. 8A and 8B wrapped around the prosthesis.

FIGS. 8A, 8B, and 9 show a third embodiment of the invention, which includes another coat or covering 300 that is a stand-alone accessory attachable to an existing valve prosthesis by an end user. A main body 310 of the covering 300 can be similar in size and shape to the main body 210 of the covering 200 in FIGS. 6 and 7, and can be made of a biocompatible cloth or other material with similar properties as those discussed with respect to the body 210 of the covering 200. A length of a central portion 311 of the body 310 of the covering 300 is sufficient for circumferentially wrapping the covering 300 around the entire prosthetic valve 1.

The covering 300 differs from the covering 200 in FIGS. 6 and 7 in the construction of the attachment mechanisms for attaching the respective coverings to the prosthetic valve 1. Rather than the loop portions 212 and the strings or threads 220, the covering 300 instead has an open first end 312 with a plurality of stringed or threaded loops 320 attached thereto.

A number and positioning of the loops 320 at the first end 312 of the covering 300 can correspond to a number and position of the apices 14 located on one end of the valve frame 10, which in the illustrated embodiment, amounts to nine total loops 320. In another embodiment, the number and positioning of the loops 320 can correspond to the number and positions of the apices 14 and the protruding ends of the commissure attachment posts 11. In yet other embodiments, the number and positioning of the loops 320 can vary and correspond, for example, to every other apex 14, or more generally, to the number and positions of the desired attachment points between the first end 312 of the covering 300 and the prosthetic valve 1, as described in greater detail below.

Meanwhile, another set of stringed or threaded loops 321 is positioned at an opposite second end 313 of the covering 300. The embodiment in FIGS. 8A to 9 includes nine loops 321 in addition to the nine loops 320 located at the first end 312, but in other embodiments, the number and positioning of the loops 321 can also be varied based generally on the positions of the desired attachment points between the second end 313 of the covering 300 and the prosthetic valve 1. In addition, the second end 313 of the covering is folded 314 and sewn or otherwise sealed together, so that loops 321 are at least partially covered or concealed within the folded cloth or material. In some embodiments, the loops 321 are covered completely by the folded portion. In other embodiments, rather than a folded portion, the loops 321 at the second end 313 of the covering 300 can instead by covered by an additional piece of cloth or material that is separately attached to the body 311 of the covering 300.

As shown in FIG. 9, the covering 300 can be wrapped or dressed around the outer surface of an existing prosthetic valve 1 by a practitioner or other end user. In this embodiment, the loops 320, 321 can be fitted over corresponding apices 14 or protruding ends of the commissure attachment posts 11 on the valve frame 10. The covered loops 321 at the second end 313 of the covering 300 can first be fitted over the apices 14 or other frame protrusions at the outflow end 3 of the prosthetic valve 1, and then the uncovered loops 321 can be fitted over the apices 14 or other frame protrusions at the inflow end 2 of the prosthetic valve 1. In another attachment method, loops 321 at the second end 313 and loops 320 at the first end 312 can be alternately attached to the prosthetic valve. Other attachment methods can, of course, also be used.

A vertical height of the covering 300 (i.e., between the first and second ends 312, 313 of the covering 300) can be slightly shorter than a height of the valve prosthesis 1, so that the covering 300 stretches in a vertical direction when the loops 321 and 320 are both attached to the frame 10, in order to form a more tight or secure connection between the valve 1 and the covering 300. Meanwhile, the loops 321 at the second end 313 are at least partially covered or concealed, so that the valve frame can be attached to the loops 321 at an inner side of the covering 300. In this manner, the second end 313 of the covering can also better conceal or cover apices and other valve frame edges at the outflow end 3 of the valve 1. Referring back to FIGS. 4A and 4B, the outflow end 3 of the valve 1 is positioned in the left ventricle 84, and will be the end of the valve 1 that comes into contact with the native mitral valve leaflets 88. Therefore, the covered loops 321 at the second end 313 of the covering 300 will be more effective in covering the apices 14 and other edges at the outflow end 3 of the valve 1 and in protecting the native valve leaflets 88 and other surrounding heart tissue from being damaged by the valve 1. On the other hand, the loops 320 at the first end 312 of the covering 300 correspond to the inflow end 2 of the valve 1, which is positioned in the left atrium 82 after implantation. Since the inflow end 2 of the valve 1 is spaced farther apart from any heart tissue, there is less concern that the apices 14 or other sharp edges at the inflow end 2 will damage the surrounding tissue. The loops 320 configured to be attached to the inflow end 2 of the valve 1 can therefore be more exposed, for example, to facilitate easier access and for easier attachment of the loops over the apices 14 and/or other protrusions at the inflow end 2 of the valve 1 by the end user. The loops 320, 321 can simply be fitted over a corresponding apex or edge of the valve frame with a single looping, or for example, each of the loops 320, 321 can be folded over to form multiple loopings around the apices for a more secure fit.

After attachment of the loops 320, 321 to the various protrusions at the ends 2, 3 of the prosthetic valve 1, in some embodiments, the end user can then further sew or otherwise more securely attach the meeting ends of the covering 300, for example, as seen in FIG. 7, to form an even more secure attachment between the covering 300 and the valve prosthesis 1. In some embodiments, ends of the covering 300 can be sewn together first, to form a tubular or substantially cylindrically shaped covering 300, into which the valve prosthesis 1 can be inserted, where attachment of the loops 321, 320 would then proceed similarly as previously discussed.

In some embodiments, the various attachment features discussed in the second embodiment of FIGS. 6 and 7 and in the third embodiment of FIGS. 8A, 8B, and 9 can be combined into a single covering, where for example, one end of the covering includes a loop portion with a string or thread similarly as discussed in the second embodiment, and the other end of the covering includes a plurality of loops to fit over protrusions at an end of the valve prosthesis 1. Various other modifications can also be envisioned based on, for example, the specific needs and desired properties of the patient and the prosthetic valve to be implanted.

In some embodiments, in addition to making attachments to an existing valve prosthesis only at the top and bottom ends of the valve, a practitioner may want to more securely attach a covering or wrap around the valve prosthesis with, for example, additional sutures or string ties at other positions on the valve frame of the prosthetic. Generally, threading strings or sutures through a valve and another layer prior to tying the layer down to the valve frame involves using a needle or other sharp tool that can pierce through the extra layer. However, use of a needle or other sharp tools around the outflow area of the valve prosthesis by an end user might lead to unintended cuts, punctures, or other damage to the valve leaflets. Such damage is also difficult to foresee or predict by the manufacturer, and can also be difficult to detect by the end user even when it occurs.

Figure 10A:
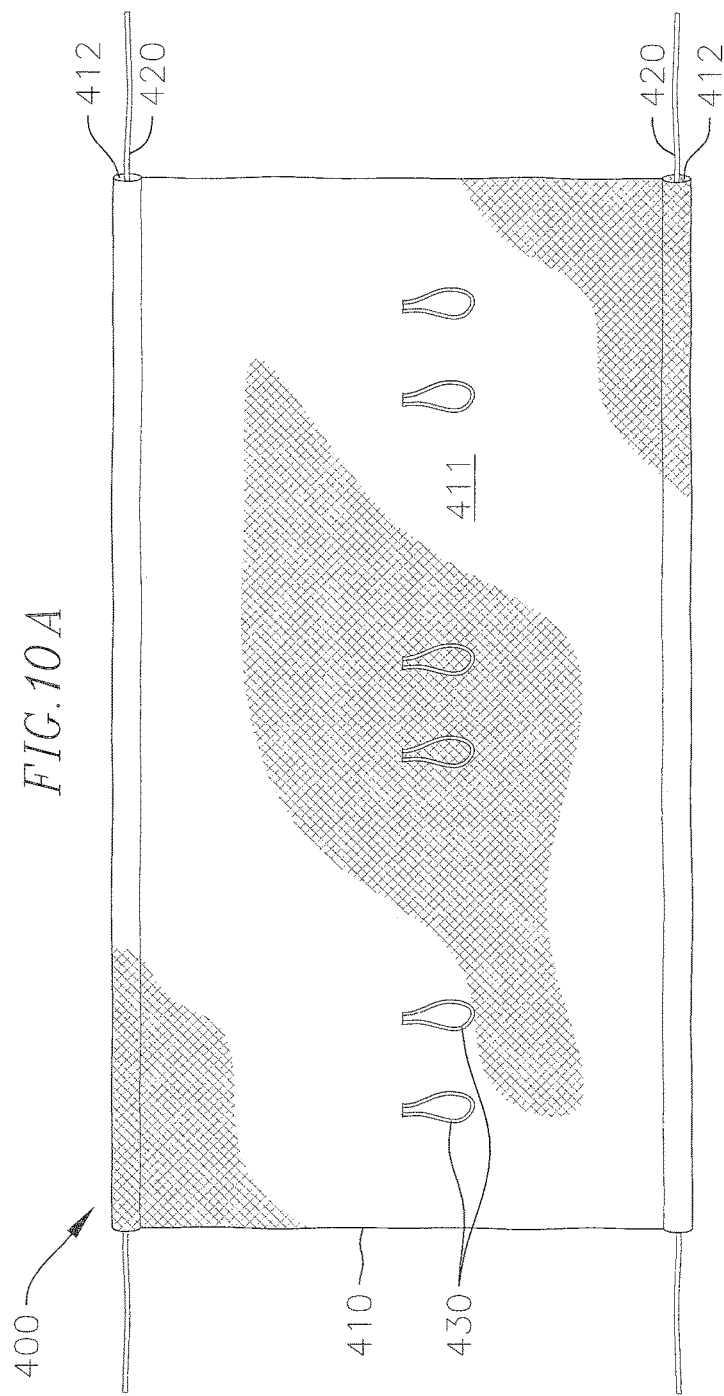
FIGS. 10A to 10C respectively show a perspective view, a close-up view, and a cross-sectional view of a portion of a covering for a heart valve according to a fourth embodiment.
Figure 10C:
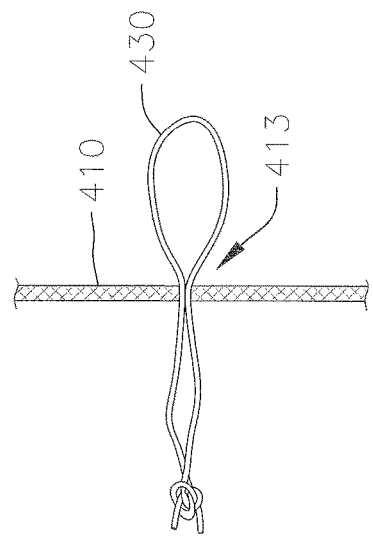
Figure 10B:
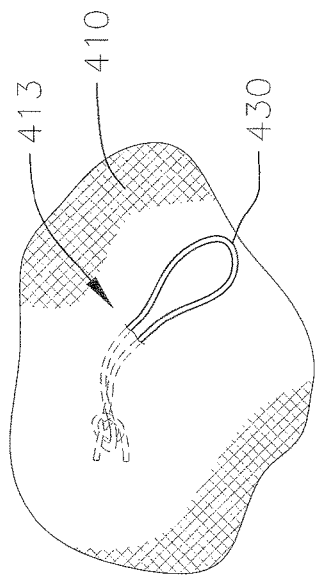

FIGS. 10A to 10C show a fourth embodiment of the invention, which includes another coat or covering 400 that is a stand-alone accessory attachable to an existing valve prosthesis by an end user. The covering 400 according to the fourth embodiment includes a plurality of pre-positioned loops that are intended to serve as a substitute for using a needle to thread or transmit strings or sutures therethrough, to aid in attaching the parts together by an end user. Sutures or strings can be threaded through the covering by first inserting the sutures through the loops on one side of the covering 400, and then pulling the loops through the covering to also transmit or thread the attached sutures through the covering 400 as well.

Referring to FIGS. 10A to 10C, a main body 410 of the covering 400 can be similar in size, shape, and construction to either the main body 210 of the covering 200 discussed in FIGS. 6 and 7, or the main body 310 of the covering 300 discussed in FIGS. 8A, 8B, and 9, or can be a combination including features from each covering. The body 400 can be made of a biocompatible cloth or other suitable material with similar properties as those previously discussed, and a length of the central portion 411 of the body 410 of the covering 400 is sufficient to wrap the covering 400 around the entire prosthetic valve 1 in a circumferential direction. In some embodiments, the covering 400 can be pre-manufactured and delivered to an end user with the side ends already sewn or otherwise attached together, such that the covering 400 is provided to the end user in a substantially cylindrical shape, as can be seen for example in FIG. 12. In other embodiments, the ends of the covering 400 can be sewn or otherwise attached together by an end user during the assembly of the covering 400 onto a prosthetic valve 1, similarly as discussed with respect to previous embodiments. For example, in the embodiment illustrated in FIG. 10A, the covering 400 includes loop portions 412 and end strings 420 that can be used to connect ends of the covering 400, similar to features discussed with respect to the covering 200 above.

The covering 400 further includes a plurality of individually threaded loops 430 that are separately threaded through the body 410 of the covering 400 during manufacturing, or at some other time prior to the covering 400 being provided to the end user. Each of the threaded loops 430 can be a separate loop made of string or of any other suitable material, and is threaded through a corresponding opening 413 at a specific position on the body 410 of the covering 400. The number and position of the openings 413 and positioning of the loops 430 corresponds to desired positions through which strings or sutures are intended to traverse through the covering 400 to facilitate attachment of the covering 400 to a frame 10 of a valve prosthesis 1. In other words, the loops 430 are positioned through openings 413 in the body 410 of the covering 400 in at least some positions (and in some cases, all of the positions) where an end user will form a connection point between the frame 10 and the covering 400. Therefore, different embodiments will include a different number of loops 430 and/or different positioning of the loops 430, based on the valve prosthesis and/or where the additional connection points are desired. In this manner, an end user can reduce or eliminate the need for a needle or other sharp tool, and thereby reduce the potential for damage caused by such a tool, during attachment of the covering 400 to the prosthetic valve 1.

Figure 11:
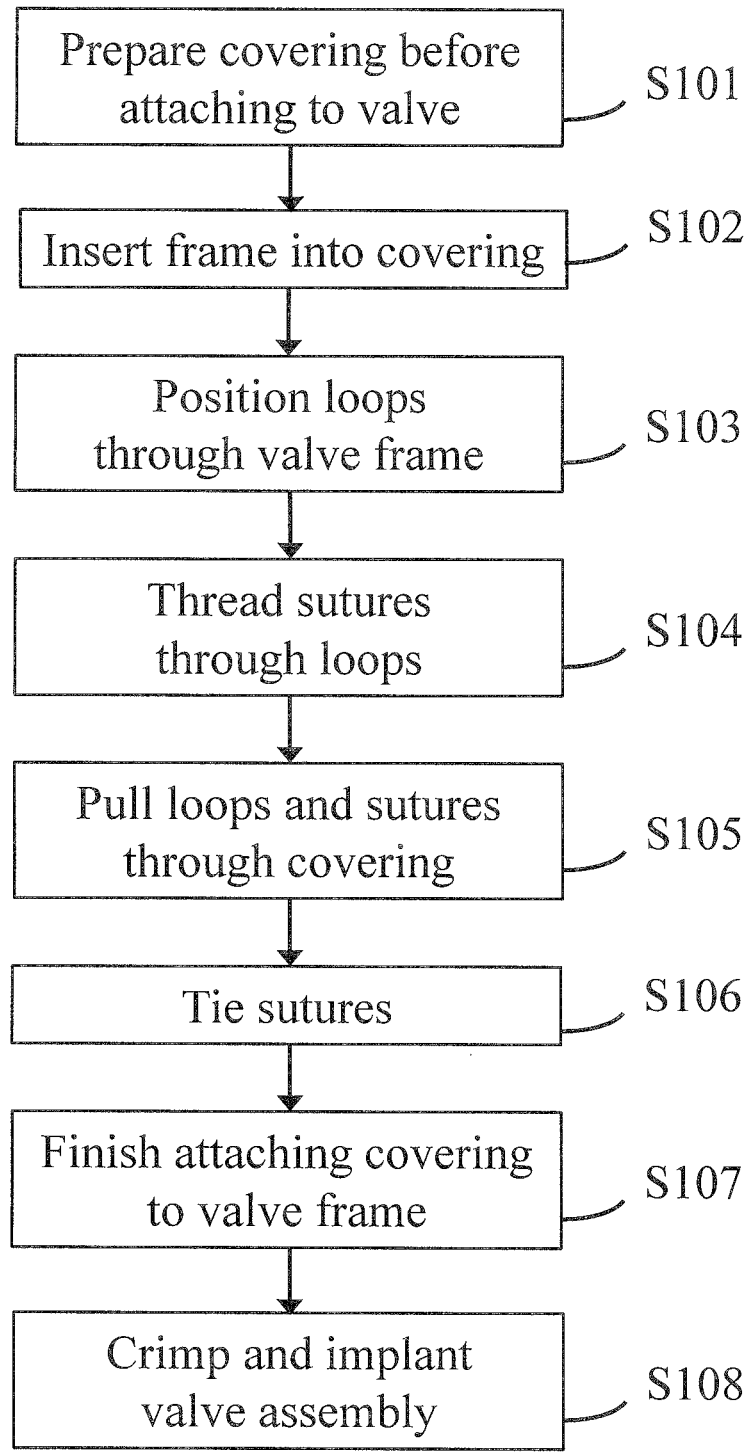
FIG. 11 is a flow chart illustrating a method of assembling the covering of FIGS. 10A-10C around a prosthetic heart valve according to the fourth embodiment of the invention.
Figure 12:
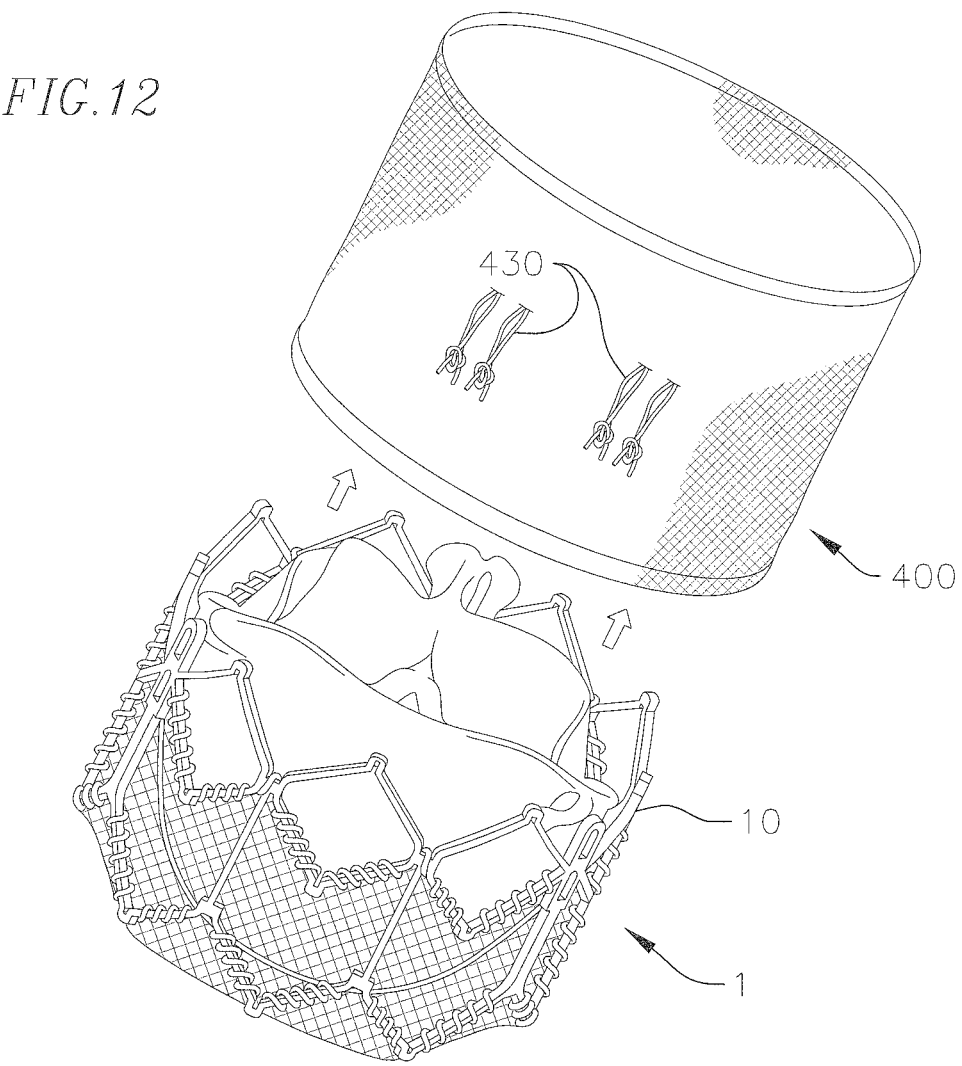
FIG. 12 shows a step of assembling the covering around a prosthetic heart valve according to the fourth embodiment.

FIG. 11 is a flow chart illustrating a method of assembling the covering 400 around a prosthetic heart valve. First, in step S101, the wrap or covering 400 is separately prepared before attaching the covering 400 to the valve 1. Generally, the covering 400 will be held in dry storage, so preparation can include, for example, removing the covering 400 from packaging and soaking the covering 400 in saline, water or other solution to soften the covering 400. In embodiments where ends of the covering 400 have not yet been joined, the end user can join the ends of the covering 400. The covering 400 can then be manipulated and adjusted or shaped into a substantially cylindrical form, as can be seen in FIG. 12. In addition, the various strings or sutures that are held in the covering 400 can be moved or adjusted to allow for easier insertion of the prosthetic valve 1 and to avoid tangling between the various strings or sutures.

In step S102, the prosthetic valve 1 is inserted into the covering 400 through one end of the covering 400 to mount the covering 400 over the valve 1, and in step S103, the loops 430 of the covering 400 are positioned through the openings in the valve frame 10 at desired locations (e.g., a separate loop 430 can be positioned on each side of a strut or apex around which a suture is to be tied). In one embodiment, the loops 430 are positioned around select middle apices of the valve frame 10 that are located around the outflow end 3 of the valve 1. In some embodiments, end attachment features can also be utilized to attach the ends of the covering 400 over or around the ends of the valve frame 10. Such attachment features can be similar to those discussed with respect to the second or third embodiments above, or can include various other end attachment methods, and can be employed before, during, or after positioning of the loops 430. Generally, the pieces of string or suture associated with end attachment will be trimmed and discarded prior to using the additional loops 430.

Figure 13:
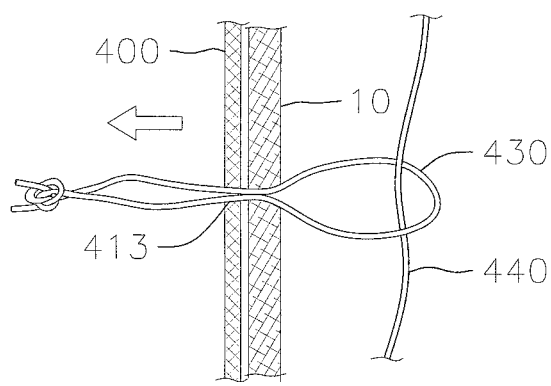
FIG. 13 shows a step of attaching the covering around the prosthetic heart valve according to the fourth embodiment.

In step S104, and as can be seen in FIG. 13, tie down threads or sutures 440 are inserted through the loops 430 at an inner side of valve frame 10. The size of the portions of the loops 430 located on the inner side of the valve frame are large enough to facilitate easy insertion of the threads or sutures 440 through the loops 430 by an end user, without the use of any additional tools.

Figure 14:
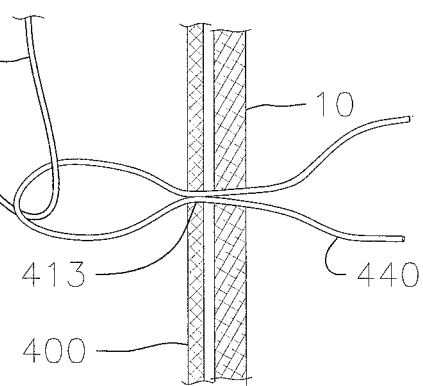
FIG. 14 shows another step of attaching the covering around the prosthetic heart valve according to the fourth embodiment.

In step S105, and as can be seen in FIG. 14, while the threads or sutures 440 are threaded through the loops 430, each of the loops 430 is pulled from the outside of the covering 400 radially away from the covering 400 until the loops 430 are separated or detached from the body 410 of the covering 400. In this manner, each of the sutures 440 is pulled with its corresponding loop 430 through the covering 400, and the sutures 440 can now be accessed from the outside of the assembly, without the use of a threading needle or other sharp tool. After threading or transferring a portion of a suture 440 through the covering 400, the corresponding loop 430 can be detached from the suture 440 and discarded. In some embodiments, it can also be desirable to thread or transfer a suture 440 from an outer side of the assembly through the covering 400 to an inner side of the assembly. The loops 430 can be utilized to facilitate transfer of sutures 440 in this direction as well. After the sutures 440 have been threaded through the covering 400 at the desired positions, and the loops 430 have been discarded, the end user can also verify that none of the strings are tangled before proceeding.

In step S106, the sutures 440 are tied down 441 (see FIG. 15) at the corresponding connection points using any appropriate tying or suturing technique, to more securely attach the covering 400 to the valve frame 10, and the excess strings or sutures can be trimmed away. In some embodiments, the sutures 440 can be individually tied down around desired struts, posts, or apices of the valve frame 10, while in other embodiments, more complex tying or suturing methods can be employed, for example, to also interweave separate sutures 440 or to apply a single suture 440 around multiple struts and/or apices of the valve frame 10. The type of attachment method utilized can be varied based on the properties of the covering 400 and the valve 1, and the level of attachment between the covering 400 and the valve frame 10 desired by the practitioner. In other embodiments, additional sutures are more sparingly applied, and these embodiments can include or incorporate use of a smaller number of loops 430, to simplify the assembly process for the end user, and for example, to reduce possibility of the strings or sutures crossing or tangling.

Figure 15:
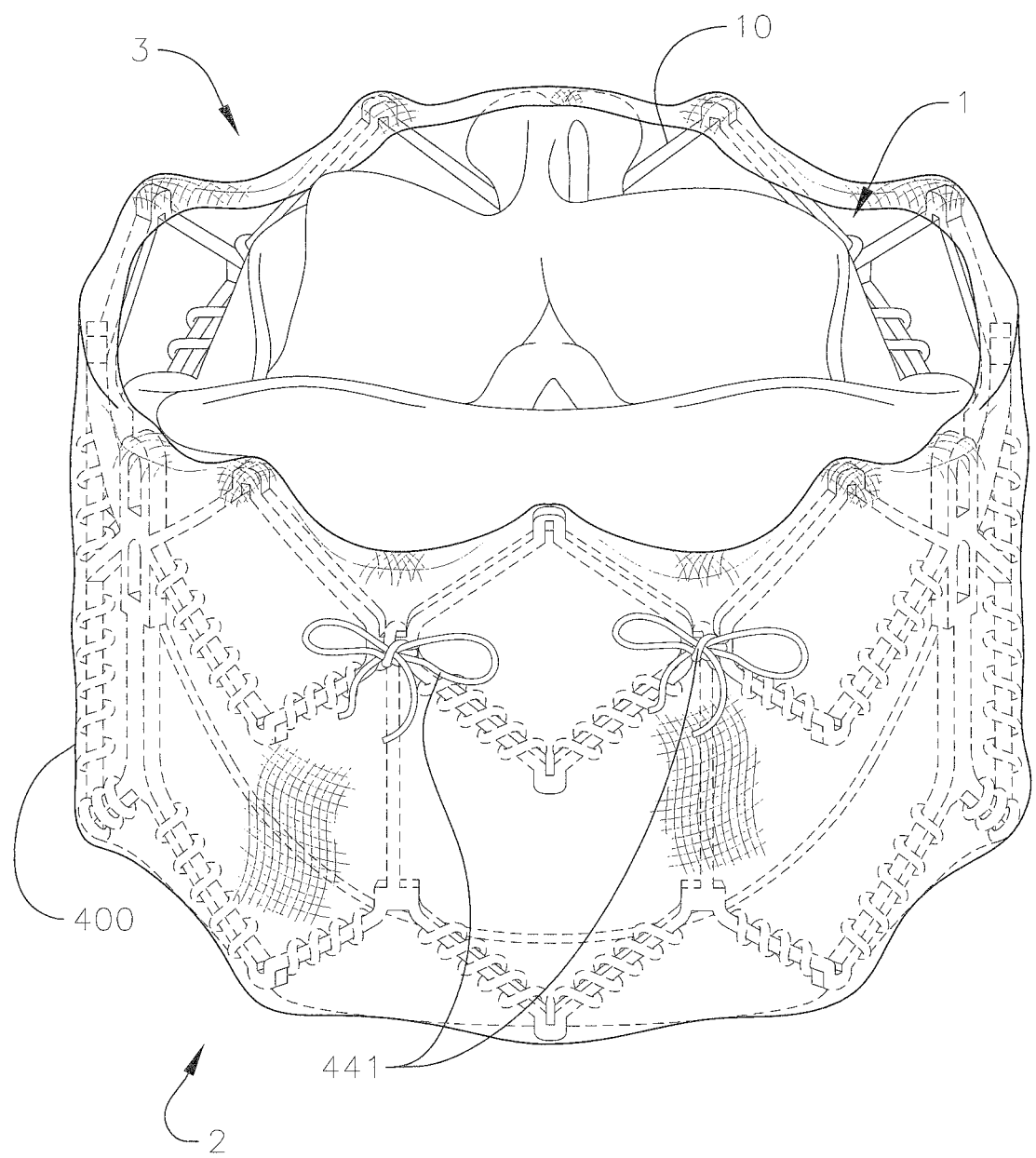
FIG. 15 shows a perspective view of a prosthetic heart valve with the covering of FIG. 10A wrapped around the prosthesis.

In step S107, final preparation of the valve assembly prior to implantation is performed. For example, the positioning of the covering 400 on the valve 1 can be checked and verified, and minor adjustments can be made to the position of the covering 400, to ensure that the apices 14, portions of the commissure attachment posts 11 that form protrusions, and any other ends or edges of the valve frame 10 are positioned correctly in pockets of the covering 400 and/or are otherwise adequately concealed or covered by the covering 400. Meanwhile, the previously discussed end attachments can also be supplemented. For example, as the loops 430 are generally employed for the portion of the covering positioned around the outflow end 3 of the valve 1, the practitioner can go back to the inflow end 2 of the valve 1, to ensure that the covering 400 is still correctly positioned at inflow end 2 after the sutures 440 have been applied at the outflow end 3. In some embodiments, additional sutures can also be made at the inflow end to further supplement the connection. The sutures at the inflow end 2 can in some instances be made using a needle or other sharp tool, since the sutures are made through the skirt 30 rather than the leaflet tissue 20, and so damage to the leaflet tissue 20 at the inflow end 2 is less likely. An example of a completed valve assembly, with a prosthetic valve 1 wrapped by a covering 400, is illustrated in FIG. 15. The tied down sutures 441 are exaggerated in FIG. 15 for clarity, and to illustrate example positions of the additional suture connections between the valve frame 10 and the covering 400.

In step S108, the covered valve assembly can be mounted onto a delivery system and crimped to prepare the valve assembly for implantation into a patient. Due to the addition of the covering 400, crimping of the valve assembly can be modified to avoid damaging covering 400 or detachment of the covering 400 from the valve 1. In one embodiment, the valve 1 is pre-crimped to an intermediate size (e.g., to a 24 mm outer diameter) before attachment of the covering 400 over the valve 1, and is then crimped to its final crimped state after attaching the covering 400. The fully crimped valve 1 with the covering 400 can then be delivered to the implant site.

Using a covering with loops according to the fourth embodiment can reduce the time it takes to thread or transmit sutures from one side of the valve frame and covering to the other side of the valve frame and covering. Furthermore, the suturing process becomes easier and quicker for the end user, because the sutures only need be threaded through the large loops instead of through an eye of a needle or other sharp threading tool, and use of sharp tools around the valve leaflet tissue is no longer necessary, eliminating the possibility of unintended damage to the leaflets caused by any such sharp tools, and thereby improving the overall performance of the implanted valves in general. In addition, since the loops are threaded through and pre-positioned on the covering during manufacturing, accuracy of the through holes for the sutures can be pre-set, leading to more accurate placement of the sutures and less errors.

While the above embodiments better protect the tissue surrounding the prosthetic valve implant from being damaged by the edges or abrasive surfaces of the implant, other issues can still arise both during and after implantation of the valve prosthesis at the mitral position. For example, during deployment and expansion of the valve prosthesis, the prosthesis generally comes into contact with the native mitral valve leaflets and/or the chordae tendineae, and in some instances, comes directly into contact with the ring or coil anchor, before the valve is fully expanded. Further expansion of the valve inside the ring or coil anchor after such contact will therefore apply outwardly directed radial pressure against, and slightly expand, the ring or coil anchor as well, leading to circumferential shifting or sliding between the valve frame and the ring or coil anchor. This can subject the native valve tissue or other heart tissue sandwiched between the valve frame and the anchor to abrasion oriented damage in the circumferential direction. Furthermore, after implantation of the valve prosthesis, typical pressures applied to the valve during regular heart cardiac cycles can also induce small movements of the valve in an axial direction relative to the ring or coil anchor, which can also cause accelerated wear of the tissue sandwiched between the valve frame and the anchor. Even with coverings similar to those discussed in previous embodiments, these issues may not be fully alleviated, since if the coatings or wraps are applied tightly to an outer surface of the prosthetic valve, friction can still occur between the coating or wrap, the ring or coil anchor, and any tissue sandwiched therebetween, which can still lead to damage to the sandwiched native tissue.

Figure 16:
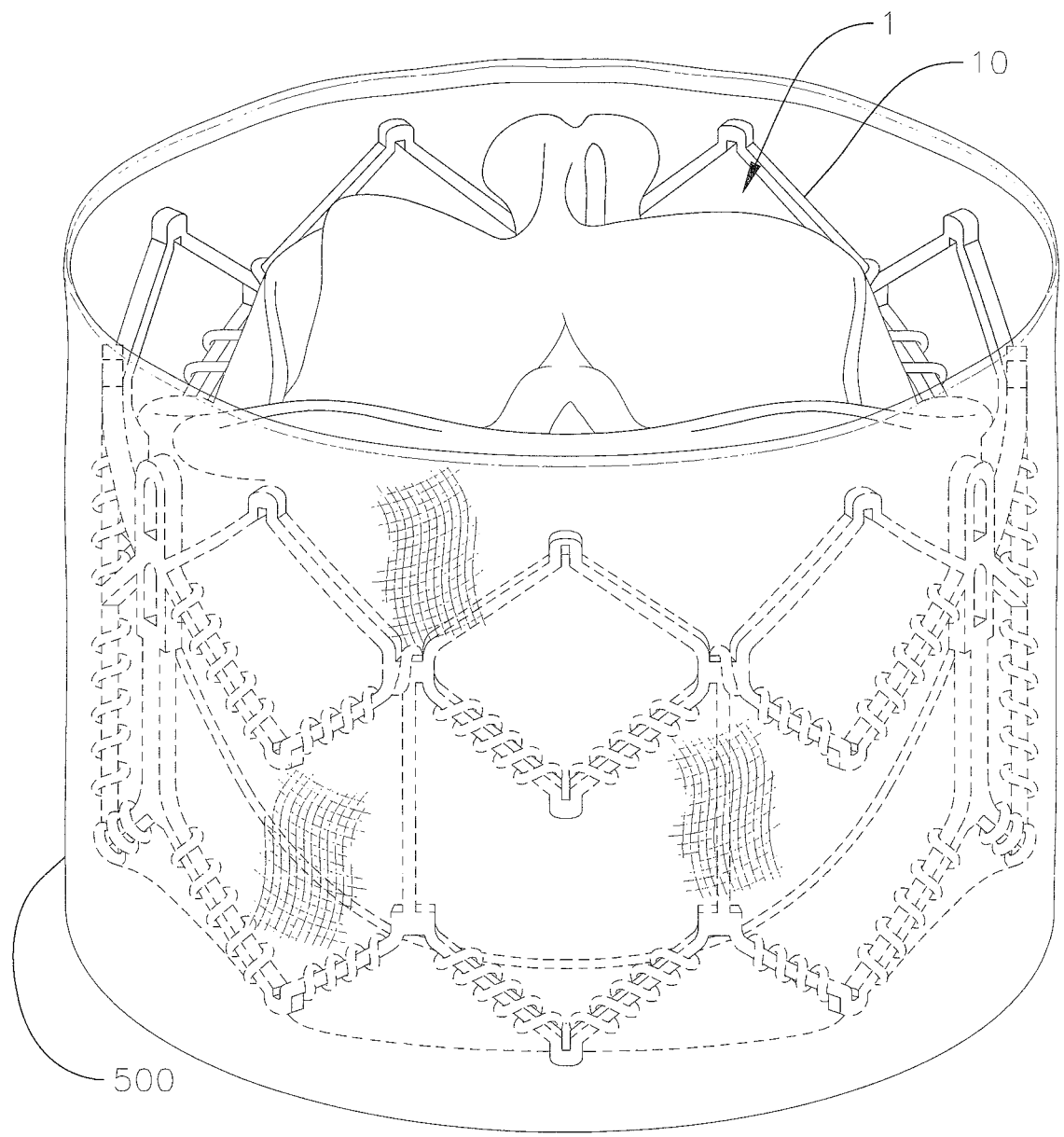
FIG. 16 shows a perspective view of a prosthetic heart valve with a covering according to a fifth embodiment wrapped around the prosthesis.

FIG. 16 shows a fifth embodiment of the invention, which includes another coat or covering 500. In some embodiments, the covering 500 is attached to the prosthetic valve 1 during the manufacturing process, but in other embodiments, the covering 500 can be modified to be a stand-alone accessory that is attachable to an existing valve prosthesis by an end user. The covering 500 is configured to wrap around and to cover substantially the entire valve frame 10. The covering 500 can be made of a biocompatible cloth or other material with similar properties as those discussed in the previous embodiments.

The covering 500 in FIG. 16 differs from previously discussed embodiments in that the covering 500 is a dual layer covering, where a first layer of cloth can be tightly attached to and around the valve frame 10, while a second layer of cloth rests on an outer surface of the first layer of cloth. A cross-section of the two layers of covering 500 is more clearly illustrated in FIGS. 17 and 18. In one arrangement, the two layer covering can be formed by a tubular body that is attached at the free ends. In another arrangement, two separate layers of cloth can be stacked and then sewn or otherwise attached together, where the two layers are sized and attached in a manner that facilitates easy sliding movement between the layers. The first or inner layer of the covering can be attached to the valve frame in a tight manner, while the second or outer layer of the covering can be arranged or attached on an outer surface of the first layer more loosely, or in any other way that allows the second layer to slide, at least to a limited extent, relative to the first layer.

Figure 17:
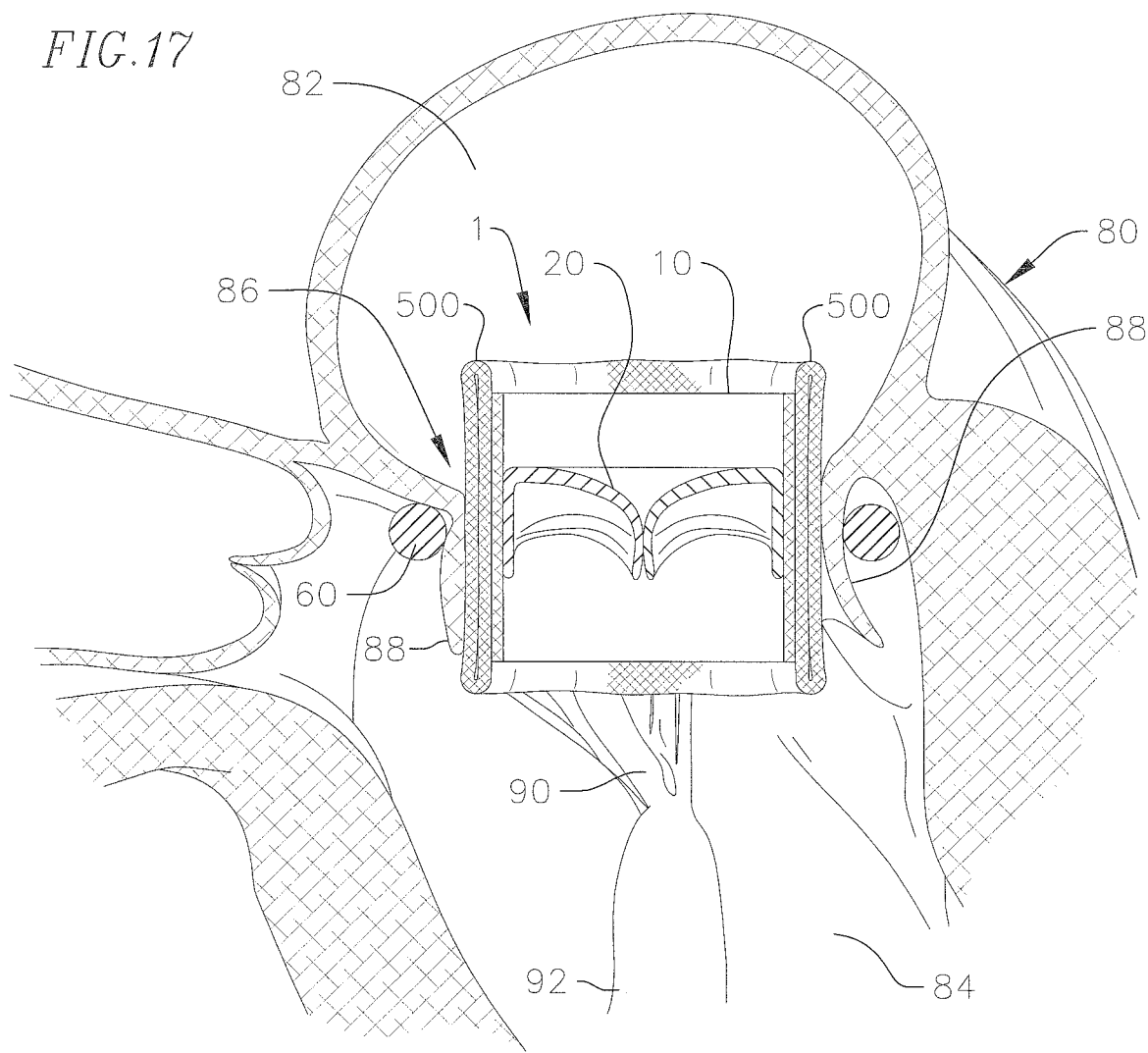
FIG. 17 shows a side cross-sectional view of a ring anchor deployed in a mitral position of the heart, with an implanted valve prosthesis covered by the covering according to the fifth embodiment.
Figure 18:
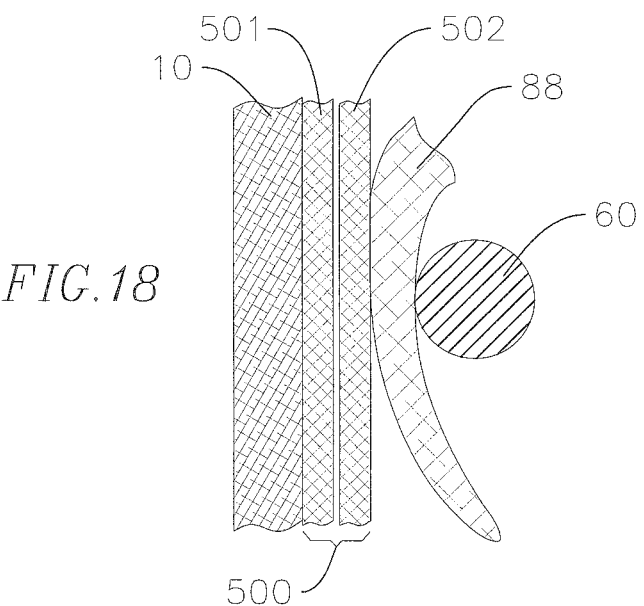
FIG. 18 is an enlarged cross-sectional view of a portion of FIG. 17, showing a close-up of one side of the implanted valve prosthesis with the covering according to the fifth embodiment.

FIGS. 17 and 18 more clearly illustrate the interactions between the two layers of the dual-layer covering 500 according to the fifth embodiment. FIG. 17 illustrates a prosthetic valve with the covering 500 deployed in a ring anchor 60 positioned around native leaflets 88 of a mitral valve 86, similarly as seen in FIG. 4A. A similar covered valve can also be used together with coil anchor 70 discussed with respect to FIG. 4B, or with any other similar anchor. As can be seen in FIG. 17, the covering 500 is noticeably longer than the prosthetic valve 1 in the axial direction, such that portions of the covering 500 extend axially away from ends of the valve 1 in one or both directions.

FIG. 18 shows a close-up cross-sectional view of one side of the valve frame 10, the anchor 60, and a portion of the native mitral valve leaflets 88 sandwiched therebetween. A first layer 501 of the covering 500 is attached to an outer surface of the valve frame 10, using one of various attachment methods, for example, any of the attachment methods discussed in the previous embodiments. Meanwhile, a second layer 502 of the covering 500 is positioned on an outer surface of the first layer 501, and also comes into contact with and is pushed up against the native mitral valve leaflets 88, the chordae tendineae, and/or other surrounding native heart tissue. Some portions of the second layer 502 of the covering 500 can also directly contact the anchor 60. Radial outward pressure applied by the expanded prosthetic valve 1 against the covering 500, the anchor 60, and the sandwiched tissue 88 causes a frictional attachment of the second layer 502 against the tissue and/or the anchor 60, such that relative movement between the second layer 502 with the tissue and/or the anchor 60 is minimized or prevented. Meanwhile, a sliding plane or interface is formed between the first layer 501 and the second layer 502 of the covering 500, where sliding between the layers 501, 502 is still permitted, and can be facilitated, for example, by an additional layer or substance added between the first layer 501 and the second layer 502 that reduces friction, or for example, by selecting a material for the covering where layers of the material slide easily against one another, or by any other suitable means.

The first layer 501 of the covering 500 remains affixed or pushed up against an outer surface of the valve frame 10, while the second layer 502 of the covering 500 remains generally affixed or pushed up against the native valve or other heart tissue 88 and/or the anchor 60. When micro movements or other small movements between the valve prosthesis 1 and the anchor 60 occurs in any direction, the two layers 501, 502 of the covering 500 slide against one another, thereby absorbing the movements of the valve 1 relative to the anchor 60 and the sandwiched tissue 88. In this manner, relative movement between the tissue 88 and each of the parts of the implant with which it comes into contact (e.g., the second layer 502, the anchor 60, etc.) is minimized or eliminated, so that abrasive conditions due to friction or other rubbing or movement against the tissue 88 will also be minimized, and thereby reducing damage to the tissue 88. Using a dual layer covering 500 according to the fifth embodiment can therefore isolate and protect the tissue 88 sandwiched between the valve 1 and the anchor 60 from small movements that could cause abrasive pressure, movement driven wear, and/or other similar damage to the tissue 88.

In other embodiments, various features from the different embodiments discussed above can also be combined into a single valve prosthesis, or into a stand-alone wrap or covering that can be assembled onto a valve prosthesis by an end user. In addition, various other modifications or alternative configurations can be made to the valve prostheses and/or the stand-alone wraps or coverings according to the above described embodiments of the invention. For example, the attachment features and/or methods for attaching the covering to the prosthetic valves can be modified to attach to different prosthetic valves or to different parts of the same valves, or for example, the single and dual layer coverings can be manufactured in different ways and using different materials from those discussed above. The covered valves can also be used together with other types of rings or anchors, other parts or features that define a bore or space into which the valve expands, or in some cases, the valves can be implanted directly in the native valve annuli without any additional anchors or other structural supporting parts or features.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art.

In view of the many possible embodiments to which the principles of the disclosure can be applied, it should be recognized that the illustrated embodiments are only preferred examples and should not be taken as limiting the scope of the disclosure. Rather, the scope of the disclosure is defined by the following claims.

What is claimed is:

1. A valve prosthesis, comprising:
a radially expandable and collapsible frame and a plurality of valve leaflets positioned at least partially in the frame and configured to control blood flow through the valve prosthesis, wherein the frame has a first end defining an outflow end, a second end defining an inflow end, and an outer surface extending from the first end to the second end; and
a covering disposed around the outer surface of the frame and connected to the frame, the covering comprising loop portions extending along the inflow and outflow ends of the frame, the loop portions defining passageways extending along the loop portions, the covering further comprising a plurality of pre-positioned strings, threads, or sutures held in the loop portions such that the covering and the plurality of pre-positioned strings, threads, or sutures comprise a standalone accessory that is attachable to and separable from the frame by the plurality of pre-positioned strings, threads, or sutures, wherein the covering comprises a fold at least at the outflow end of the frame, and covers substantially all of the outer surface of the frame.

2. The valve prosthesis of claim 1, wherein the covering covers the first end, the second end, and the entire outer surface of the frame.

3. The valve prosthesis of claim 1, wherein the covering comprises pericardial tissue.

4. The valve prosthesis of claim 1, wherein the plurality of pre-positioned strings, threads, or sutures are held between a first covering layer and a second layer of the covering forming the loop portions.

5. The valve prosthesis of claim 1, wherein the covering extends beyond the outflow end of the frame such that the fold is located downstream of and axially spaced apart from the outflow end of the frame.

6. The valve prosthesis of claim 1, wherein:
the covering comprises a first edge adjacent the outflow end of the frame and a second edge adjacent the inflow end of the frame; and
the covering is folded over the outflow end of the frame such that the first edge of the covering is disposed inside the frame.

7. The valve prosthesis of claim 1, wherein the covering comprises a cloth layer.

8. The valve prosthesis of claim 1, wherein two ends of the covering are attached to one another such that the covering forms a tubular structure.

9. A prosthetic heart valve, comprising:
a radially expandable and collapsible frame having an inflow end and an outflow end;
a plurality of valve leaflets positioned at least partially in the frame and configured to control blood flow through the prosthetic heart valve; and
a covering disposed around the frame and connected to the frame, the covering comprising loop portions extending along the inflow and outflow ends of the frame, the loop portions defining passageways extending along the loop portions, the covering further comprising a string, thread, or suture pre-positioned in each loop portion such that the covering and the pre-positioned strings, threads, or sutures comprise a standalone accessory that is attachable to and separable from the frame by the pre-positioned strings, threads, or sutures.

10. The prosthetic heart valve of claim 9, wherein the loop portions comprise top and bottom edges of the covering folded over and connected to the covering to form overlapping regions that define the passageways.

11. The prosthetic heart valve of claim 9, wherein ends of the pre-positioned strings, threads, or sutures are tied together to connect the covering to the frame.

12. The prosthetic heart valve of claim 11, wherein the pre-positioned strings, threads, or sutures are tightened so that the covering forms perimeters at the inflow and outflow ends of the frame that are smaller than the inflow and outflow ends of the frame.

13. The prosthetic heart valve of claim 12, wherein apices of the frame at the inflow end of the frame and apices of the frame at the outflow end of the frame are covered by the covering.

14. The prosthetic heart valve of claim 9, wherein meeting ends of the covering are sutured together to form a seam extending between the loop portions.

15. The prosthetic heart valve of claim 14, wherein the seam extends between a first knot formed by a pre-positioned string, thread, or suture tied at the inflow end of the frame and a second knot formed by a pre-positioned string, thread, or suture tied at the outflow end of the frame.

16. A valve prosthesis, comprising:
a radially expandable and collapsible frame and a plurality of valve leaflets positioned at least partially in the frame and configured to control blood flow through the valve prosthesis, wherein the frame has a first end defining an outflow end, a second end defining an inflow end, and an outer surface extending from the first end to the second end; and
a covering disposed around the outer surface of the frame and connected to the frame, the covering comprising a plurality of pre-positioned strings, threads, or sutures coupled to the covering such that the covering and the plurality of pre-positioned strings, threads, or sutures comprise a standalone accessory that is attachable to and separable from the frame by the plurality of pre-positioned strings, threads, or sutures, wherein the covering comprises a fold at least at the outflow end of the frame, and covers substantially all of the outer surface of the frame;

wherein the covering comprises a first layer attached to the frame and a second layer positioned on an outer surface of the first layer and configured to slide or move along the outer surface of the first layer.

\* \* \* \* \*